United States Patent
Patane et al.

(10) Patent No.: US 6,214,832 B1
(45) Date of Patent: Apr. 10, 2001

(54) BIS-PIPERIDINYL-PYRIMIDIN-2-ONES AS ALPHA 1A ADRENERGIC RECEPTOR ANTAGONISTS

(75) Inventors: Michael A. Patane, Harleysville; Mark G. Bock, Hatfield, both of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/099,660

(22) Filed: Jun. 17, 1998

Related U.S. Application Data

(60) Provisional application No. 60/050,126, filed on Jun. 18, 1997.

(51) Int. Cl.$^7$ .................... C01D 461/14; C07D 413/14; A61K 31/513; A61K 31/519; A61P 31/08
(52) U.S. Cl. .................. 514/258; 514/259; 514/274; 544/278; 544/280; 544/284; 544/316
(58) Field of Search ................. 544/278, 280, 544/284, 316; 514/274, 258, 259

(56) References Cited

U.S. PATENT DOCUMENTS

| | | | |
|---|---|---|---|
| 4,661,491 | 4/1987 | Regnier | 514/260 |
| 4,769,371 | 9/1988 | Atwal | 544/58.5 |
| 4,847,379 | 7/1989 | Atwal | 544/316 |
| 4,855,301 | 8/1989 | Atwal et al. | 514/269 |
| 5,202,330 | 4/1993 | Atwal et al. | 514/274 |
| 5,574,044 | 11/1996 | Thompson et al. | 514/316 |
| 5,618,827 | 4/1997 | Oxford | 514/326 |

FOREIGN PATENT DOCUMENTS

| | | |
|---|---|---|
| 0 234 830 | 9/1987 | (EP) . |
| 0 236 902 | 9/1987 | (EP) . |

(List continued on next page.)

OTHER PUBLICATIONS

W. C. Wong et al., "Design and Synthesis of Dihydropyrimidines as Alpha 1a Adrenoceptor Selective Antagonists", Abstract No. MEDI 064, 215th ACS National Meeting, Dallas, TX (Mar. 29–Apr. 2, 1998).

(List continued on next page.)

Primary Examiner—Mukund J. Shah
Assistant Examiner—Thomas McKenzie
(74) Attorney, Agent, or Firm—Catherine D. Fitch; Kenneth R. Walton; Melvin Winokur

(57) ABSTRACT

Pyrimidinone, oxazolidinone, and (alkyl)aryl derivatives, their synthesis, and their use as alpha 1a adrenergic receptor antagonists are disclosed. One application of these compounds is in the treatment of benign prostatic hyperplasia. These compounds are selective in their ability to relax smooth muscle tissue enriched in the alpha 1a receptor subtype without at the same time inducing hypotension. One such tissue is found surrounding the urethral lining.

Therefore, one utility of the instant compounds is to provide acute relief to males suffering from benign prostatic hyperplasia, by permitting less hindered urine flow. Another utility of the instant compounds is provided by combination with a human 5-alpha reductase inhibitory compound, such that both acute and chronic relief from the effects of benign prostatic hyperplasia are achieved. Among the disclosed derivatives are piperidinyl aminoalkylpiperidinyl pyrimidinones, including those of formula:

wherein Q is $R^1$ is selected from unsubstituted, mono- or poly-substituted phenyl wherein the substituents on the phenyl are independently selected from halogen, $CF_3$, cyano, nitro, $N(R^7)_2$, $NR^7COR^{19}$, $NR^7CON(R^{19})_2$, $NR^7SO_2R^{19}$, $NR^7SO_2N(R^{19})_2$, $OR^6$, $(CH_2)_{0-4}CO_2R^7$, $(CH_2)_{0-4}CON(R^7)_2$, or $C_{1-4}$ alkyl; or unsubstituted, mono- or poly-substituted pyridyl, pyrazinyl, thienyl, thiazolyl, furanyl, quinazolinyl or naphthyl wherein the substituents on the pyridyl, pyrazinyl, thienyl, thiazolyl, furanyl, quinazolinyl or naphthyl are independently selected from $CF_3$, cyano, nitro, amino, $(CH_2)_{0-4}CO_2R^7$, $(CH_2)_{0-4}CON(R^7)_2$, $(CH_2)_{0-4}SO_2N(R^7)_2$, $(CH_2)_{0-4}SO_2R^6$, phenyl, $OR^6$, halogen, $C_{1-4}$ alkyl or $C_{3-8}$ cycloalkyl;

m and p are each integers from zero to two, wherein the sum m+p=2; n and o are each integers from zero to two, wherein the sum n+o=2; q is an integer of from zero to three, provided that when q is zero, $R^{26}$ is hydrogen; s is an integer of from zero to four; and E, G, J, L, M, W, X, $R^2$, $R^3$, $R^4$, $R^5$, $R^6$, $R^7$, $R^8$, $R^{11}$, $R^{12}$, $R^{13}$, $R^{14}$, $R^{15}$, $R^{16}$, $R^{19}$ and $R^{26}$ are defined herein.

13 Claims, No Drawings

FOREIGN PATENT DOCUMENTS

| | | |
|---|---|---|
| 1329617 | 5/1963 | (FR) . |
| 92/00073 | 1/1992 | (WO) . |
| 92/16213 | 10/1992 | (WO) . |
| 94/08040 | 4/1994 | (WO) . |
| 94/10989 | 5/1994 | (WO) . |
| 94/22829 | 10/1994 | (WO) . |
| 96/14846 | 5/1996 | (WO) . |
| 97/17969 | 5/1997 | (WO) . |
| 97/42956 | 11/1997 | (WO) . |

OTHER PUBLICATIONS

B. Lagu et al., "Design Synthesis and Evaluation of Dihydropyrimidinones as Alpha 1a Selective Antagonists", Abstract No., MEDI 065, 215th ACS National Meeting, Dallas, TX (Mar. 29–Apr. 2, 1998).

D. Nagarathnam et al., "Design, Synthesis and Evaluation of Dihydropyrimidinones as Alpha 1a Selective Antagonists: 6. Synthesis and Structure–Activity Relationship of SNAP 6553 and Analogs", Abstract No. MEDI 066, 215th ACS National Meeting, Dallas, TX (Mar. 29–Apr. 2, 1998).

M. R. Marzabadi et al, "Design, Synthesis and evaluation of Dihydropyrimidinones and Dihyfropyrimidines as Alpha 1a Selective Antagonists: Modification of the Diarylpiperidine Moiety", Abstract No. MEDI 067, 215th ACS National Meeting, Dallas, TX (Mar. 29–Apr. 2, 1998).

Derwent CPI Abstracts No. 90–041598, "Remedy for Dysuria", Abstract of JP01–319418, Nippon Chemifar (1990).

Derwent CPI Abstracts No. 87–027600, "New 1,3–oxazolidin–2–one derivatives", Abstract of JP61–286375, Nippon Chemifar (1987).

G. C. Rovnyak et al., "Dihydropyrimidine Calcium Channel Blockers. 4. Basic 3–Substitutued–4–aryl–1, 4–dihydropyrimidine–5–carboxylic Acid Esters. Potent Antihypertensive Agents", J. Med. Chem., 35 (17), 3254–63 (1992).

K. S. Atwal et al., "Dihydropyrimidine Calcium Channel Blockers. 3. 3–Carbamoyl–4–aryl–1,2,3, 4–tetrahydro–6–methyl–5–pyrimidinecarboxylic Acid Esters as Orally Effective Antihypertensive Agents", J. Med. Chem., 34(2), 806–11 (1991).

K. S. Atwal et al., "Dihydropyrimidine Calcium Channel Blockers. 2. 3–Substituted–4–aryl–1, 4–dihydro–6–methyl–5–pyrimidinecarboxylic Acid Esters as Potent Mimics of Dihydropyridines", J. Med. Chem., 33(9), 2629–35 (1990).

K. S. Atwal et al., "Substituted 1,4–Dihydropyrimidines. 3. Synthesis of Selectively Functionalized 2–Hetero–1,4–dihydropyrimidines", J. Org. Chem., 54(25), 5898–907 (1989).

BIS-PIPERIDINYL-PYRIMIDIN-2-ONES AS ALPHA 1A ADRENERGIC RECEPTOR ANTAGONISTS

This application claims the benefit of U.S. Provisional Application Ser. No. 60/050,126, filed Jun. 18, 1997.

FIELD OF THE INVENTION

This invention relates to certain novel compounds and derivatives thereof, their synthesis, and their use as alpha 1a adrenoceptor antagonists. More particularly, the compounds of the present invention are useful for treating benign prostatic hyperplasia (BPH).

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors bind norepinephrine more strongly than epinephrine and much more strongly than the synthetic compound isoproterenol. The binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into alpha 1, alpha 2, $\beta_1$, and $\beta_2$ subtypes. Functional differences between alpha 1 and alpha 2 receptors have been recognized, and compounds which exhibit selective binding between these two subtypes have been developed.

For a general background on the alpha adrenergic receptors, the reader's attention is directed to Robert R. Ruffolo, Jr., *a-Adrenoreceptors: Molecular Biology. Biochemistry and Pharmacology*, (*Progress in Basic and Clinical Pharmacology* series, Karger, 1991), wherein the basis of alpha 1/alpha 2 subclassification, the molecular biology, signal transduction (G-protein interaction and location of the significant site for this and ligand binding activity away from the 3'-terminus of alpha adrenergic receptors), agonist structure-activity relationships, receptor functions, and therapeutic applications for compounds exhibiting alpha-adrenergic receptor affinity was explored.

The cloning, sequencing and expression of alpha receptor subtypes from animal tissues has led to the subclassification of the alpha 1 receptors into alpha 1d (formerly known as alpha 1a or 1a/1d), alpha 1b and alpha 1a (formerly known as alpha 1c) subtypes. Each alpha 1 receptor subtype exhibits its own pharmacologic and tissue specificities. The designation "alpha 1a" is the appellation recently approved by the IUPHAR Nomenclature Committee for the previously designated "alpha 1c" cloned subtype as outlined in the 1995 Receptor and Ion Channel Nomenclature Supplement (Watson and Girdlestone, 1995). The designation alpha 1a is used throughout this application to refer to this subtype. At the same time, the receptor formerly designated alpha 1a was renamed alpha 1d. The new nomenclature is used throughout this application. Stable cell lines expressing these alpha 1 receptor subtypes are referred to herein; however, these cell lines were deposited with the American Type Culture Collection (ATCC) under the old nomenclature. For a review of the classification of alpha 1 adrenoceptor subtypes, see, Martin C. Michel, et al., *Naunyn-Schmiedeberg's Arch. Pharmacol.* (1995) 352:1–10.

The differences in the alpha adrenergic receptor subtypes have relevance in pathophysiologic conditions. Benign prostatic hyperplasia, also known as benign prostatic hypertrophy or BPH, is an illness typically affecting men over fifty years of age, increasing in severity with increasing age. The symptoms of the condition include, but are not limited to, increased difficulty in urination and sexual dysfunction. These symptoms are induced by enlargement, or hyperplasia, of the prostate gland. As the prostate increases in size, it impinges on free-flow of fluids through the male urethra. Concomitantly, the increased noradrenergic innervation of the enlarged prostate leads to an increased adrenergic tone of the bladder neck and urethra, further restricting the flow of urine through the urethra.

In benign prostatic hyperplasia, the male hormone 5alpha-dihydrotestosterone has been identified as the principal culprit. The continual production of 5a-dihydrotestosterone by the male testes induces incremental growth of the prostate gland throughout the life of the male. Beyond the age of about fifty years, in many men, this enlarged gland begins to obstruct the urethra with the pathologic symptoms noted above.

The elucidation of the mechanism summarized above has resulted in the recent development of effective agents to control, and in many cases reverse, the pernicious advance of BPH. In the forefront of these agents is Merck & Co., Inc's product PROSCAR® (finasteride). The effect of this compound is to inhibit the enzyme testosterone 5-a reductase, which converts testosterone into 5a-dihydrotesterone, resulting in a reduced rate of prostatic enlargement, and often reduction in prostatic mass.

The development of such agents as PROSCAR® bodes well for the long-term control of BPH. However, as may be appreciated from the lengthy development of the syndrome, its reversal also is not immediate. In the interim, those males suffering with BPH continue to suffer, and may in fact lose hope that the agents are working sufficiently rapidly.

In response to this problem, one solution is to identify pharmaceutically active compounds which complement slower-acting therapeutics by providing acute relief. Agents which induce relaxation of the lower urinary tract tissue, by binding to alpha 1 adrenergic receptors, thus reducing the increased adrenergic tone due to the disease, would be good candidates for this activity. Thus, one such agent is alfuzosin, which is reported in EP 0 204597 to induce urination in cases of prostatic hyperplasia. Likewise, in WO 92/0073, the selective ability of the R(+) enantiomer of terazosin to bind to adrenergic receptors of the alphai subtype was reported. In addition, in WO 92/161213, combinations of 5a-reductase inhibitory compounds and alpha1-adrenergic receptor blockers (terazosin, doxazosin, prazosin, bunazosin, indoramin, alfuzosin) were disclosed. However, no information as to the alpha 1d, alpha 1b, or alpha 1a subtype specificity of these compounds was provided as this data and its relevancy to the treatment of BPH was not known. Current therapy for BPH uses existing non-selective alpha 1 antagonists such as prazosin (Minipress, Pfizer), Terazosin (Hytrin, Abbott) or doxazosin mesylate (Cardura, Pfizer). These non-selective antagonists suffer from side effects related to antagonism of the alpha 1d and alpha 1b receptors in the peripheral vasculature, e.g., hypotension and syncope.

The recent cloning of the human alpha 1a adrenergic receptor (ATCC CRL 11140) and the use of a screening assay utilizing the cloned human alpha 1a receptor enables identification of compounds which specifically interact with the human alpha 1a adrenergic receptor. [PCT International Application Publication Nos. WO94/08040, published April 14, 1994 and WO94/10989, published May 26, 1994] As disclosed in the instant patent disclosure, a cloned human alpha 1a adrenergic receptor and a method for identifying compounds which bind the human alpha 1a receptor has now made possible the identification of selective human alpha 1a adrenergic receptor antagonists useful for treating BPH. The instant patent disclosure discloses novel compounds which selectively bind to the human alpha 1a receptor. These compounds are further tested for binding to other human alpha 1 receptor subtypes, as well as counter-screened against other types of receptors (e.g., alpha 2), thus defining the specificity of the compounds of the present invention for the human alpha 1a adrenergic receptor.

It is an object of the present invention to identify compounds which bind to the alpha 1a adrenergic receptor. It is a further object of the invention to identify compounds which act as antagonists of the alpha 1a adrenergic receptor. It is another object of the invention to identify alpha 1a adrenergic receptor antagonist compounds which are useful agents for treating BPH in animals, preferably mammals, especially humans. Still another object of the invention is to identify alpha 1a adrenergic receptor antagonists which are useful for relaxing lower urinary tract tissue in animals, preferably mammals, especially humans.

It has now been found that the compounds of the present invention are alpha 1a adrenergic receptor antagonists. Thus, the compounds of the present invention are useful for treating BPH in mammals. Additionally, it has been found that the alpha 1a adrenergic receptor antagonists of the present invention are also useful for relaxing lower urinary tract tissue in mammals.

SUMMARY OF THE INVENTION

The present invention provides compounds for the treatment of urinary obstruction caused by benign prostatic hyperplasia (BPH). The compounds antagonize the human alpha 1a adrenergic receptor at nanomolar and subnanomolar concentrations while exhibiting at least ten fold lower affinity for the alpha 1d and alpha 1b human adrenergic receptors and many other G-protein coupled receptors. This invention has the advantage over non-selective alpha 1 adrenoceptor antagonists of reduced side effects related to peripheral adrenergic blockade. Such side effects include hypotension, syncope, lethargy, etc. The compounds of the present invention have the structure:

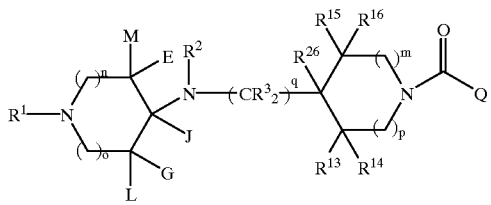

wherein Q is selected from

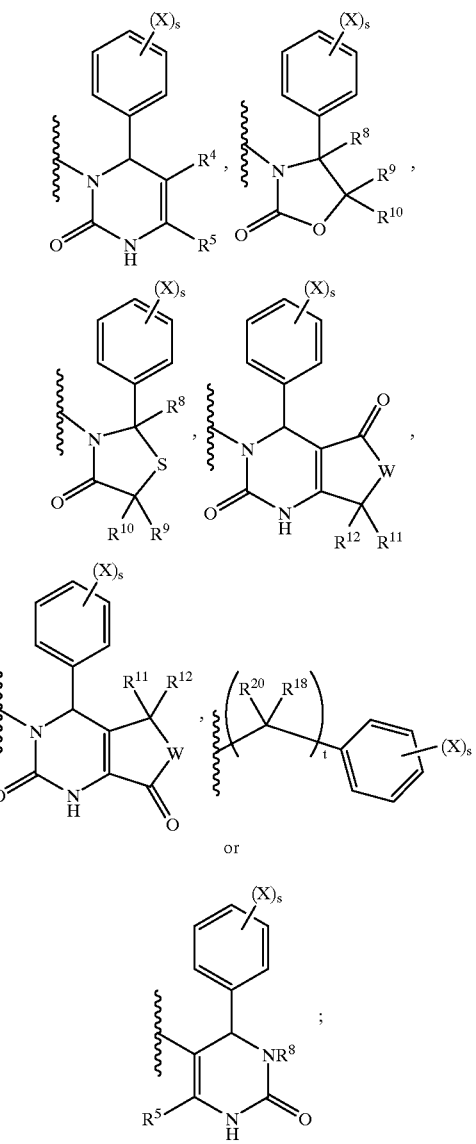

or $R^1$ is selected from unsubstituted, mono- or poly-substituted phenyl wherein the substituents on the phenyl are independently selected from halogen, $CF_3$, cyano, nitro, $N(R^7)_2$, $NR^7COR^{19}$, $NR^7CON(R^{19})_2$, $NR^7SO_2R^{19}$, $NR^7SO_2N(R^{19})_2$, $OR^6$, $(CH_2)_{0-4}CO_2R^7$, $(CH_2)_{0-4}CON(R^7)_2$, or $C_{1-4}$ alkyl; or unsubstituted, mono- or poly-substituted pyridyl, pyrazinyl, thienyl, thiazolyl, furanyl, quinazolinyl or naphthyl wherein the substituents on the pyridyl, pyrazinyl, thienyl, thiazolyl, furanyl, quinazolinyl or naphthyl are independently selected from $CF_3$, cyano, nitro, amino, $(CH_2)_{0-4}CO_2R^7$, $(CH_2)_{0-4}CON(R^7)_2$, $(CH_2)_{0-4}SO_2N(R^7)_2$, $(CH_2)_{0-4}SO_2R^6$, phenyl, $OR^6$, halogen, $C_{1-4}$ alkyl or $C_{3-8}$ cycloalkyl;

E, G, L and M are each independently selected from hydrogen, $C_{1-8}$ alkyl, $C_{3-8}$ cycloalkyl, $(CH_2)_{0-4}OR^6$, $(CH_2)_{0-4}N(R^7)_2$, $(CH_2)_{0-4}CN$, $(CH_2)_{0-4}CF_3$, $(CH_2)_{0-4}CO_2R^7$, $(CH_2)_{0-4}CON(R^7)_2$, $(CH_2)_{0-4}SO_2R^7$, or $(CH_2)_{0-4}SO_2N(R^7)_2$;

J is selected from hydrogen, $C_{1-8}$ alkyl, $C_{3-8}$ cycloalkyl, $(CH_2)_{1-4}OR^6$, $(CH_2)_{1-4}N(R^7)_2$, $(CH_2)_{1-4}CN$, $(CH_2)_{0-4}CF_3$, $(CH_2)_{0-4}CO_2R^7$, $(CH_2)_{0-4}CON(R^7)_2$, $(CH_2)_{0-4}SO_2R^7$, or $(CH_2)_{0-4}SO_2N(R^7)_2$;

$R^2$ is independently selected from hydrogen, $C_{1-8}$ alkyl, $C_{4-8}$ cycloalkyl, $(CH_2)_{0-4}CO_2R^7$, $(CH_2)_{0-4}CON(R^7)_2$, $(CH_2)_{0-4}COR^7$, $(CH_2)_{2-4}OR^6$, $(CH_2)_{1-4}CF_3$, $(CH_2)_{0-4}SO_2R^7$, $(CH_2)_{0-4}SO_2N(R^7)_2$ or $(CH_2)_{1-4}CN$;

$R^3$, $R^8$, $R^9$, $R^{10}$, $R^{14}$, $R^{15}$ and $R^{16}$ are each independently selected from hydrogen, $C_{1-8}$ alkyl, $C_{3-8}$ cycloalkyl, $(CH_2)_{2-4}OR^6$ or $(CH_2)_{0-4}CF_3$;

$R^4$ is selected from hydrogen, $(CH_2)_{0-4}COR^6$, $(CH_2)_{0-4}CN$, $(CH_2)_{0-4}CF_3$, $(CH_2)_{0-4}CO_2R^7$, $(CH_2)_{0-4}CON(R^7)_2$, $(CH_2)_{0-4}SO_2R^6$, or $(CH_2)_{0-4}SO_2N(R^7)_2$;

$R^5$ is selected from hydrogen, $C_{1-8}$ alkyl, $C_{3-8}$ cycloalkyl, $(CH_2)_{1-4}OR^6$ or $(CH_2)_{0-4}CF_3$;

$R^6$ is selected from hydrogen, $C_{1-8}$ alkyl, $C_{3-8}$ cycloalkyl or $(CH_2)_{0-4}CF_3$;

$R^7$ and $R^{19}$ are each independently selected from hydrogen, $C_{1-8}$ alkyl, $C_{4-8}$ cycloalkyl or $(CH_2)_{1-4}CF_3$;

$R^{11}$ and $R^{12}$ are each independently selected from hydrogen, $C_{1-8}$ alkyl or $C_{3-8}$ cycloalkyl;

$R^{13}$ is selected from hydrogen, $C_{1-8}$ alkyl, $C_{3-8}$ cycloalkyl, $(CH_2)_{2-4}OR^6$, $OR^6$ or $(CH_2)_{0-4}CF_3$;

$R^{18}$ is selected from hydrogen, $C_{1-8}$ alkyl, $C_{3-8}$ cycloalkyl, $(CH_2)_{1-4}OR^6$, $(CH_2)_{0-4}CF_3$, unsubstituted, mono- or poly-substituted phenyl wherein the substituents on the phenyl are independently selected from halogen, $CF_3$, cyano, nitro, $CO_2R^7$, $OR^6$, $(CH_2)_{0-4}CON(R^7)_2$, $(CH_2)_{0-4}CO_2R^7$ or $C_{1-4}$ alkyl; or unsubstituted, mono- or poly-substituted: pyridyl, pyrazinyl, thienyl, furanyl or naphthyl wherein the substituents on the pyridyl, pyrazinyl, thienyl, furanyl or naphthyl are independently selected from $CF_3$, phenyl, $OR^6$, halogen, $C_{1-4}$ alkyl or $C_{3-8}$ cycloalkyl;

$R^{20}$ is selected from hydrogen, $C_{1-8}$ alkyl, $C_{3-8}$ cycloalkyl, $(CH_2)_{0-4}OR^6$ or $(CH_2)_{0-4}CF_3$;

W is O or $NR^{11}$;

$R^{26}$ is selected from hydrogen or $OR^{28}$;

$R^{28}$ is selected from hydrogen, $C_{1-8}$ alkyl, $C_{3-8}$ cycloalkyl, $(CH_2)_{2-4}OR^6$ or $(CH_2)_{0-4}CF_3$;

X is selected from halogen, cyano, nitro, $C_{1-8}$ alkyl, $C_{3-8}$ cycloalkyl, $(CH_2)_{0-4}OR^6$ or $(CH_2)_{0-4}CF_3$ m, p and q are each independently an integer of from zero to three, provided that when q is zero, $R^{26}$ is hydrogen;

n, o, s and t are each independently an integer of from zero to four;

and the pharmaceutically acceptable salts thereof.

In a first embodiment of the invention are compounds having the structure

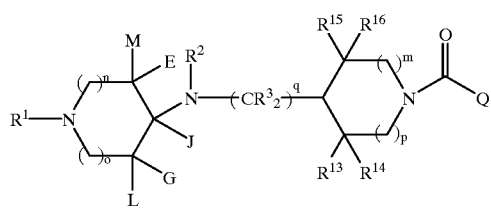

wherein $R^4$ is selected from $(CH_2)_{0-4}COR^6$, $(CH_2)_{0-4}CN$, $(CH_2)_{0-4}CF_3$, $(CH_2)_{0-4}CO_2R^7$, $(CH_2)_{0-4}CON(R^7)_2$, $(CH_2)_{0-4}SO_2R^6$, or $(CH_2)_{0-4}SO_2N(R^7)_2$;

$R^{13}$ is selected from hydrogen, $C_{1-8}$ alkyl, $C_{3-8}$ cycloalkyl, $(CH_2)_{2-4}OR^6$ or $(CH_2)_{0-4}CF_3$;

and all other variables are as previously defined; and the pharmaceutically acceptable salts thereof.

In a second embodiment of the instant invention is the compound of the formula:

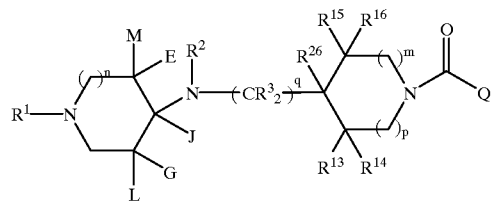

wherein Q is selected from

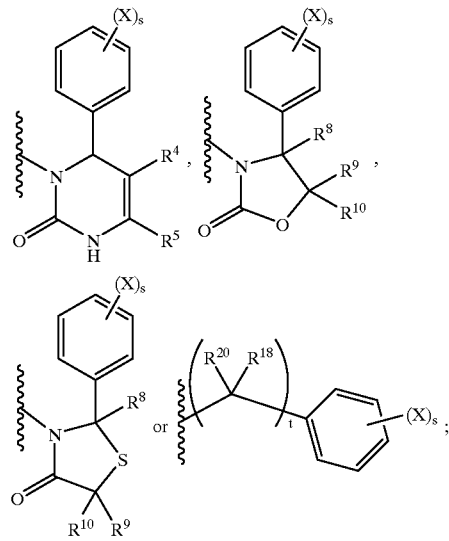

$R^1$ is selected from unsubstituted, mono-, di- or tri-substituted phenyl wherein the substituents on the phenyl are independently selected from halogen, $CF_3$, cyano, nitro, $N(R^7)_2$, $NR^7COR^{19}$, $NR^7CON(R^{19})_2$, $NR^7SO_2R^{19}$, $NR^7SO_2N(R^{19})_2$, $OR^6$, $(CH_2)_{0-4}CO_2R^7$, $(CH_2)_{0-4}CON(R^7)_2$, or $C_{1-4}$ alkyl; or unsubstituted, mono-, di- or tri-substituted pyridyl, pyrazinyl, thienyl, thiazolyl, furanyl, quinazolinyl or naphthyl wherein the substituents on the pyridyl, pyrazinyl, thienyl, thiazolyl, furanyl, quinazolinyl or naphthyl are independently selected from $CF_3$, cyano, nitro, amino, $(CH_2)_{0-4}CO_2R^7$, $(CH_2)_{0-4}CON(R^7)_2$, $(CH_2)_{0-4}SO_2N(R^7)_2$, $(CH_2)_{0-4}SO_2R^6$, phenyl, $OR^6$, halogen, $C_{1-4}$ alkyl or $C_{3-8}$ cycloalkyl;

E, G, L, M and J are each independently selected from hydrogen, $C_{1-8}$ alkyl, $C_{3-8}$ cycloalkyl, or $(CH_2)_{0-4}CF_3$;

$R^2$ is selected from hydrogen, $C_{1-8}$ alkyl, $C_{4-8}$ cycloalkyl or $(CH_2)_{1-4}CF_3$;

$R^3$, $R^8$, $R^9$, $R^{10}$, $R^{14}$, $R^{15}$ and $R^{16}$ are each independently selected from hydrogen, $C_{1-6}$ alkyl, $C_{3-6}$ cycloalkyl, $(CH_2)_{2-4}OR^6$ or $(CH_2)_{0-4}CF_3$;

$R^{13}$ is selected from hydrogen, $C_{1-6}$ alkyl, $C_{3-6}$ cycloalkyl, $(CH_2)_{2-4}OR^6$, $OR^6$ or $(CH_2)_{0-4}CF_3$;

$R^{18}$ is selected from hydrogen, $C_{1-8}$ alkyl, $C_{3-8}$ cycloalkyl, $(CH_2)_{1-4}OR^6$, $(CH_2)_{0-4}CF_3$, unsubstituted, mono-, di- or tri-substituted phenyl wherein the substituents on the phenyl are independently selected from halogen, $CF_3$, cyano, nitro, $CO_2R^7$, $OR^6$, $(CH_2)_{0-4}CON(R^7)_2$, $(CH_2)_{0-4}CO_2R^7$ or $C_{1-4}$ alkyl; or unsubstituted, mono-, di- or tri-substituted: pyridyl, pyrazinyl, thienyl, furanyl or naphthyl wherein the substituents on the pyridyl, pyrazinyl, thienyl, furanyl or naphthyl are independently selected from $CF_3$, phenyl, $OR^6$, halogen, $C_{1-4}$ alkyl or $C_{3-8}$ cycloalkyl; and $R^{20}$ is selected from hydrogen, $C_{1-6}$ alkyl, $C_{3-6}$ cycloalkyl, $(CH_2)_{0-4}OR^6$ or $(CH_2)_{0-4}CF_3$;

$R^{28}$ is selected from hydrogen, $C_{1-6}$ alkyl, $C_{3-6}$ cycloalkyl, $(CH_2)_{2-4}OR^6$ or $(CH_2)_{0-4}CF_3$;

m, n and p are each independently an integer from zero to two, provided that when q is zero, $R^{28}$ is hydrogen; and all other variables are as originally defined; and the pharmaceutically acceptable salts thereof.

In a third embodiment of the instant invention is the compound of the formula:

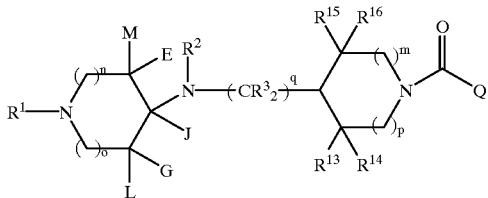

wherein Q is selected from

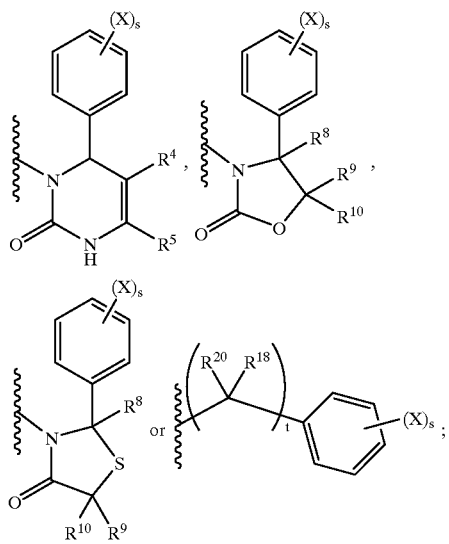

$R^1$ is selected from unsubstituted, mono-, di- or tri-substituted phenyl wherein the substituents on the phenyl are independently selected from halogen, $CF_3$, cyano, nitro, $N(R^7)_2$, $NR^7COR^{19}$, $NR^7CON(R^{19})_2$, $NR^7SO_2R^{19}$, $NR^7SO_2N(R^{19})_2$, $OR^6$, $(CH_2)_{0-4}CO_2R^7$, $(CH_2)_{0-4}CON(R^7)_2$, or $C_{1-4}$ alkyl; or unsubstituted, mono-, di- or tri-substituted pyridyl, pyrazinyl, thienyl, thiazolyl, furanyl, quinazolinyl or naphthyl wherein the substituents on the pyridyl, pyrazinyl, thienyl, thiazolyl, furanyl, quinazolinyl or naphthyl are independently selected from $CF_3$, cyano, nitro, amino, $(CH_2)_{0-4}CO_2R^7$, $(CH_2)_{0-4}CON(R^7)_2$, $(CH_2)_{0-4}SO_2N(R^7)_2$, $(CH_2)_{0-4}SO_2R^6$, phenyl, $OR^6$, halogen, $C_{1-4}$ alkyl or $C_{3-8}$ cycloalkyl;

E, G, L, M and J are each independently selected from hydrogen, $C_{1-8}$ alkyl, $C_{3-8}$ cycloalkyl, or $(CH_2)_{0-4}CF_3$;

$R^2$ is selected from hydrogen, $C_{1-8}$ alkyl, $C_{4-8}$ cycloalkyl or $(CH_2)_{1-4}CF_3$;

$R^3$, $R^8$, $R^9$, $R^{10}$, $R^{13}$, $R^{14}$, $R^{15}$ and $R^{16}$ are each independently selected from hydrogen, $C_{1-6}$ alkyl, $C_{3-6}$ cycloalkyl, $(CH_2)_{2-4}OR^6$ or $(CH_2)_{0-4}CF_3$;

$R^{18}$ is selected from hydrogen, $C_{1-8}$ alkyl, $C_{3-8}$ cycloalkyl, $(CH_2)_{1-4}OR^6$, $(CH_2)_{0-4}CF_3$, unsubstituted, mono-, di- or tri-substituted phenyl wherein the substituents on the phenyl are independently selected from halogen, $CF_3$, cyano, nitro, $CO_2R^7$, $OR^6$, $(CH_2)_{0-4}CON(R^7)_2$, $(CH_2)_{0-4}CO_2R^7$ or $C_{1-4}$ alkyl; or unsubstituted, mono-, di- or tri-substituted: pyridyl, pyrazinyl, thienyl, furanyl or naphthyl wherein the substituents on the pyridyl, pyrazinyl, thienyl, furanyl or naphthyl are independently selected from $CF_3$, phenyl, $OR^6$, halogen, $C_{1-4}$ alkyl or $C_{3-8}$ cycloalkyl; and $R^{20}$ is selected from hydrogen, $C_{1-6}$ alkyl, $C_{3-6}$ cycloalkyl, $(CH_2)_{0-4}OR^6$ or $(CH_2)_{0-4}CF_3$;

m, n and p are each independently an integer from zero to two; and all other variables are as defined previously in the first embodiment; and the pharmaceutically acceptable salts thereof.

In a first class of the invention is the compound of the formula

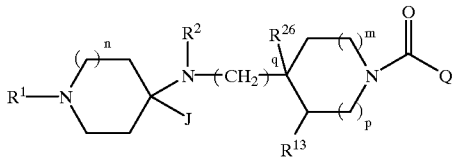

wherein Q is selected from

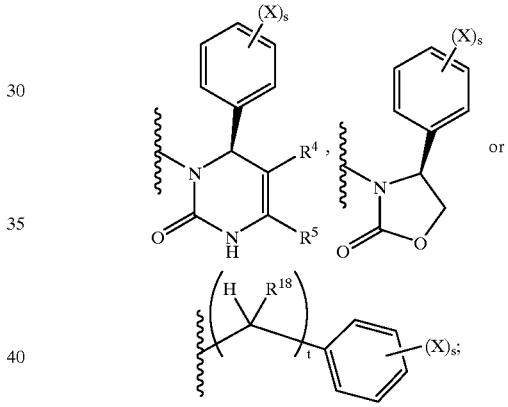

$R^1$ is selected from unsubstituted, mono-, di or tri-substituted phenyl wherein the substituents on the phenyl are independently selected from halogen, $CF_3$, cyano, nitro, $N(R^7)_2$, $OR^6$, $(CH_2)_{0-2}CO_2R^7$, $(CH_2)_{0-2}CON(R^7)_2$, or $C_{1-4}$ alkyl; or unsubstituted, mono- or di-substituted pyridyl wherein the substituents are independently selected from halogen, $CF_3$, cyano, nitro, amino, $OR^6$, $CO_2R^7$, $CON(R^7)_2$ or $C_{1-4}$ alkyl;

$R^2$ is selected from hydrogen, $C_{1-6}$ alkyl, $C_{4-6}$ cycloalkyl or $(CH_2)_{1-4}CF_3$;

$R^4$ is selected from hydrogen, $COR^6$, $(CH_2)_{0-2}CO_2R^7$, $SO_2R^6$ or $(CH_2)_{0-2}CON(R^7)_2$;

$R^5$ is selected from hydrogen, $C_{1-6}$ alkyl, $C_{3-6}$ cycloalkyl, $(CH_2)_{1-3}OR^6$ or $(CH_2)_{0-3}CF_3$; and $R^6$ is selected from hydrogen, $C_{1-6}$ alkyl, $C_{3-6}$ cycloalkyl or $(CH_2)_{0-2}CF_3$;

$R^7$ is selected from hydrogen, $C_{1-6}$ alkyl, $C_{4-6}$ cycloalkyl or $(CH_2)_{1-2}CF_3$;

$R^{13}$ is selected from hydrogen or $OR^6$;

$R^{18}$ is selected from hydrogen, $C_{1-6}$ alkyl, $C_{3-6}$ cycloalkyl, $(CH_2)_{2-4}OR^6$, $(CH_2)_{0-2}CF_3$ or unsubstituted, mono- or di-substituted phenyl wherein the substituents on the phenyl are independently selected from halogen, $CF_3$, cyano, nitro, amino, $OR^6$, $CO_2R^7$, $CON(R^7)_2$ or $C_{1-4}$ alkyl;

$R^{26}$ is selected from hydrogen or $OR^{28}$, wherein $R^{28}$ is selected from hydrogen or $C_{1-6}$ alkyl;

m, n and p are each independently an integer from zero to one; and t is an integer from one to two;

and all other variables are as defined previously in the second embodiment;

and the pharmaceutically acceptable salts thereof

In a second class of the invention is the compound of the formula

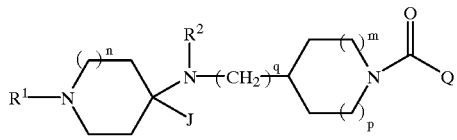

wherein Q is selected from

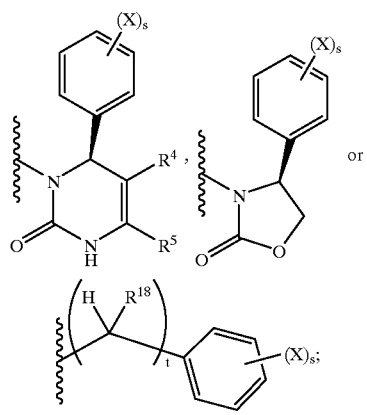

$R^1$ is selected from unsubstituted, mono-, di or tri-substituted phenyl wherein the substituents on the phenyl are independently selected from halogen, $CF_3$, cyano, nitro, $N(R^7)_2$, $OR^6$, $(CH_2)_{0-2}CO_2R^7$, $(CH_2)_{0-2}CON(R^7)_2$, or $C_{1-4}$ alkyl; or unsubstituted, mono- or di-substituted pyridyl wherein the substituents are independently selected from halogen, $CF_3$, cyano, nitro, amino, $OR^6$, $CO_2R^7$, $CON(R^7)_2$ or $C_{1-4}$ alkyl;

$R^2$ is selected from hydrogen, $C_{1-6}$ alkyl, $C_{4-6}$ cycloalkyl or $(CH_2)_{1-4}CF_3$;

$R^4$ is selected from $COR^6$, $(CH_2)_{0-2}CO_2R^7$, $SO_2R^6$ or $(CH_2)_{0-2}CON(R^7)_2$;

$R^5$ is selected from hydrogen, $C_{1-6}$ alkyl, $C_{3-6}$ cycloalkyl, $(CH_2)_{1-3}OR^6$ or $(CH_2)_{0-3}CF_3$; and $R^6$ is selected from hydrogen, $C_{1-6}$ alkyl, $C_{3-6}$ cycloalkyl or $(CH_2)_{0-2}CF_3$;

$R^7$ is selected from hydrogen, $C_{1-6}$ alkyl, $C_{4-6}$ cycloalkyl or $(CH_2)_{1-2}CF_3$;

$R^{18}$ is selected from hydrogen, $C_{1-6}$ alkyl, $C_{3-6}$ cycloalkyl, $(CH_2)_{2-4}OR^6$, $(CH_2)_{0-2}CF_3$ or unsubstituted, mono- or di-substituted phenyl wherein the substituents on the phenyl are independently selected from halogen, $CF_3$, cyano, nitro, amino, $OR^6$, $CO_2R^7$, $CON(R^7)_2$ or $C_{1-4}$ alkyl;

m, n and p are each independently an integer from zero to one;

t is an integer from one to two;

and all other variables are as defined previously in the third embodiment;

and the pharmaceutically acceptable salts thereof.

In a first subclass of the invention is the compound of the formula

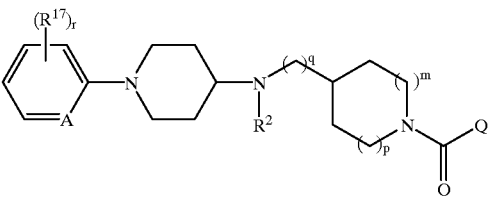

wherein A is C—$R^{17}$ or N;

$R^2$ is selected from hydrogen or $CH_2CF_3$;

$R^{13}$ is selected from hydrogen or hydroxy;

each $R^{17}$ is independently selected from hydrogen, halogen, $CF_3$, cyano, nitro, amino, $OR^6$, $CO_2R^7$, $CON(R^7)_2$ or $C_{1-4}$ alkyl;

$R^{26}$ is selected from hydrogen or hydroxy;

each X is halogen;

q and r are each independently an integer from zero to two, provided that when q is zero, $R^{26}$ is hydrogen; and s is an integer from zero to three;

and all other variables are as previously defined in the first class; and the pharmaceutically acceptable salts thereof.

In a second subclass of the invention is the compound of the formula

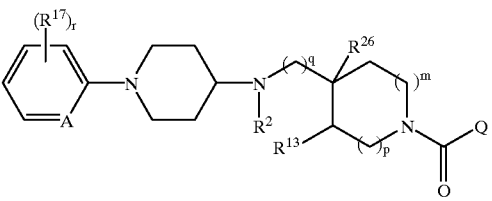

wherein A is C—$R^{17}$ or N;

$R^2$ is selected from hydrogen or $CH_2CF_3$;

each $R^{17}$ is independently selected from hydrogen, halogen, $CF_3$, cyano, nitro, amino, $OR^6$, $CO_2R^7$, $CON(R^7)_2$ or $C_{1-4}$ alkyl;

each X is halogen;

q and r are each independently an integer from zero to two; and s is an integer from zero to three;

and all other variables are as previously defined in the second class; and the pharmaceutically acceptable salts thereof.

Illustrative of the invention is the compound selected from

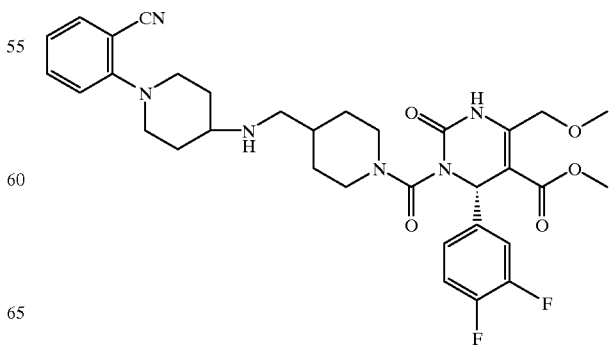

-continued
or

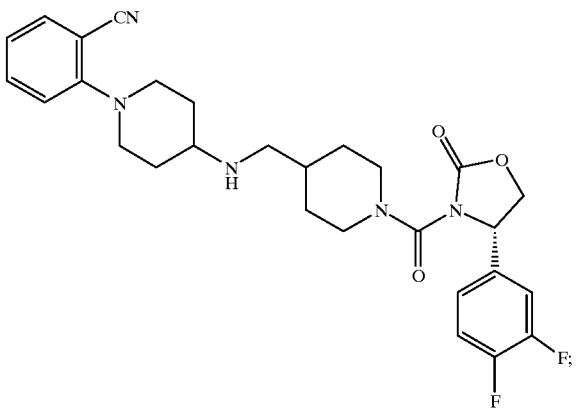

and the pharmaceutically acceptable salts thereof.

An illustration of the invention is a pharmaceutical composition comprising a therapeutically effective amount of any of the compounds described above and a pharmaceutically acceptable carrier. An example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Another example of the invention is the composition further comprising a therapeutically effective amount of a testosterone 5-alpha reductase inhibitor. Preferably, the testosterone 5-alpha reductase inhibitor is a type 1, a type 2, both a type 1 and a type 2 (i.e., a three component combination comprising any of the compounds described above combined with both a type 1 testosterone 5-alpha reductase inhibitor and a type 2 testosterone 5-alpha reductase inhibitor) or a dual type 1 and type 2 testosterone 5-alpha reductase inhibitor. More preferably, the testosterone 5-alpha reductase inhibitor is a type 2 testosterone 5-alpha reductase inhibitor. Most preferably, the testosterone 5-alpha reductase inhibitor is finasteride.

More specifically illustrating the invention is a method of treating benign prostatic hyperplasia in a subject in need thereof which comprises administering to the subject a therapeutically effective amount of any of the compounds (or any of the compositions) described above.

Further exemplifying the invention is the method of treating BPH wherein the compound (or composition) additionally does not cause a fall in blood pressure at dosages effective to alleviate BPH.

Another illustration of the invention is the method of treating benign prostatic hyperplasia wherein the compound is administered in combination with a testosterone 5-alpha reductase inhibitor. Preferably, the testosterone 5-alpha reductase inhibitor is finasteride.

Further illustrating the invention is a method of inhibiting contraction of prostate tissue or relaxing lower urinary tract tissue in a subject in need thereof which comprises administering to the subject a therapeutically effective amount of any of the compounds (or any of the compositions) described above.

More specifically exemplifying the invention is the method of inhibiting contraction of prostate tissue or relaxing lower urinary tract tissue wherein the compound (or composition) additionally does not cause a fall in blood pressures at dosages effective to inhibit contraction of prostate tissue.

More particularly illustrating the invention is the method of inhibiting contraction of prostate tissue or relaxing lower urinary tract tissue wherein the compound (or composition) is administered in combination with a testosterone 5-alpha reductase inhibitor; preferably, the testosterone 5-alpha reductase inhibitor is finasteride.

More particularly exemplifying the invention is a method of treating a disease which is susceptible to treatment by antagonism of the alpha 1a receptor which comprises administering to a subject in need thereof an amount of any of the compounds described above effective to treat the disease. Diseases which are susceptible to treatment by antagonism of the alpha 1a receptor include, but are not limited to, BPH, high intraocular pressure, high cholesterol, impotency, sympathetically mediated pain, migraine (see, K. A. Vatz, *Headache* 1997:37: 107–108) and cardiac arrhythmia.

An additional illustration of the invention is the use of any of the compounds described above in the preparation of a medicament for: a) the treatment of benign prostatic hyperplasia; b) relaxing lower urinary tract tissue; or c) inhibiting contraction of prostate tissue; in a subject in need thereof.

An additional example of the invention is the use of any of the alpha 1a antagonist compounds described above and a 5-alpha reductase inhibitor for the manufacture of a medicament for: a) treating benign prostatic hyperplasia; b) relaxing lower urinary tract tissue; or c) inhibiting contraction of prostate tissue which comprises an effective amount of the alpha 1a antagonist compound and an effective amount of 5-alpha reductase inhibitor, together or separately.

DETAILED DESCRIPTION OF THE INVENTION

Representative compounds of the present invention exhibit high selectivity for the human alpha 1a adrenergic receptor. One implication of this selectivity is that these compounds display selectivity for lowering intraurethral pressure without substantially affecting diastolic blood pressure.

Representative compounds of this invention display sub-micromolar affinity for the human alpha 1a adrenergic receptor subtype while displaying at least ten-fold lower affinity for the human alpha1d and alpha1b adrenergic receptor subtypes, and many other G-protein coupled human receptors. Particular representative compounds of this invention exhibit nanomolar and subnanomolar affinity for the human alpha 1a adrenergic receptor subtype while displaying at least 30 fold lower affinity for the human alpha1d and alpha1b adrenergic receptor subtypes, and many other G-protein coupled human receptors (e.g., serotonin, dopamine, alpha 2 adrenergic, beta adrenergic or muscarinic receptors).

These compounds are administered in dosages effective to antagonize the alpha 1a receptor where such treatment is needed, as in BPH. For use in medicine, the salts of the compounds of this invention refer to non-toxic "pharmaceutically acceptable salts." Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative pharmaceutically acceptable salts include the following:

Acetate, Benzenesulfonate, Benzoate, Bicarbonate, Bisulfate, Bitartrate, Borate, Bromide, Calcium, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isothionate, Lactate, Lactobionate, Laurate, Malate, Maleate, Mandelate, Mesylate, Methylbromide, Methylnitrate, Methylsulfate, Mucate, Napsylate, Nitrate, N-methylglucamine ammonium salt, Oleate, Pamoate (Embonate), Palmitate, Pantothenate, Phosphate/diphosphate, Polygalacturonate, Salicylate, Stearate, Sulfate, Subacetate, Succinate, Tannate, Tartrate, Teoclate, Tosylate, Triethiodide and Valerate.

Compounds of this invention are used to reduce the acute symptoms of BPH. Thus, compounds of this invention may be used alone or in conjunction with a more long-term anti-BPH therapeutics, such as testosterone 5-a reductase inhibitors, including PROSCAR® (finasteride). Aside from their utility as anti-BPH agents, these compounds may be used to induce highly tissue-specific, localized alpha 1a adrenergic receptor blockade whenever this is desired. Effects of this blockade include reduction of intra-ocular pressure, control of cardiac arrhythmias, and possibly a host of alpha 1a receptor mediated central nervous system events.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

Where the compounds according to the invention have at least one chiral center, they may accordingly exist as enantiomers. Where the compounds according to the invention possess two or more chiral centers, they may additionally exist as diastereoisomers. It is to be understood that all such isomers and mixtures thereof are encompassed within the scope of the present invention. Furthermore, some of the crystalline forms for compounds of the present invention may exist as polymorphs and as such are intended to be included in the present invention. In addition, some of the compounds of the present invention may form solvates with water (i.e., hydrates) or common organic solvents. Such solvates are also encompassed within the scope of this invention.

The term "alkyl" shall mean straight or branched chain alkanes of one to ten total carbon atoms, or any number within this range (i.e., methyl, ethyl, 1-propyl, 2-propyl, n-butyl, s-butyl, t-butyl, etc.).

The term "alkenyl" shall mean straight or branched chain alkenes of two to ten total carbon atoms, or any number within this range.

The term "aryl" as used herein, except where otherwise specifically defined, refers to unsubstituted, mono- or poly-substituted aromatic groups such as phenyl or naphthyl.

The term "cycloalkyl" shall mean cyclic rings of alkanes of three to eight total carbon atoms (i.e., cyclopropyl, cyclobutyl, cyclopentyl, cyclohexyl, cycloheptyl or cyclooctyl).

Whenever the term "alkyl" or "aryl" or either of their prefix roots appear in a name of a substituent (e.g., aralkoxyaryloxy) it shall be interpreted as including those linitations given above for "alkyl" and "aryl." Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The term "halogen" shall include iodine, bromine, chlorine and fluorine.

The term "substituted" shall be deemed to include multiple degrees of substitution by a named substituent. The term "poly-substituted" as used herein shall include di-, tri-, tetra- and penta-substitution by a named substituent. Preferably, a poly-substituted moiety is di-, tri- or tetra-substituted by the named substituents, most preferably, di- or tri-substituted.

It is intended that the definition of any substituent or variable (e.g., X, $R^6$, $R^7$, $R^{19}$) at a particular location in a molecule be independent of its definitions elsewhere in that molecule. Thus, $-N(R^{19})_2$ represents $-NH_2$, $-NHCH_3$, $-NHC_2H_5$, $-N(CH_3)C_2H_5$, etc. It is understood that substituents and substitution patterns on the compounds of the instant invention can be selected by one of ordinary skill in the art to provide compounds that are chemically stable and that can be readily synthesized by techniques known in the art as well as those methods set forth below.

Where multiple substituent moieties are disclosed or claimed, the substituted compound can be independently substituted by one or more of the disclosed or claimed substituent moieties, singly or plurally.

The term heterocycle or heterocyclic ring, as used herein, represents an unsubstituted or substituted stable 5- to 7-membered monocyclic ring system which may be saturated or unsaturated, and which consists of carbon atoms and from one to three heteroatoms selected from N, O or S, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, and oxadiazolyl. Morpholino is the same as morpholinyl.

The terms "(+)-DHP" and "DHP" as used herein, refers to a dihydropyrimidinone group of the formula

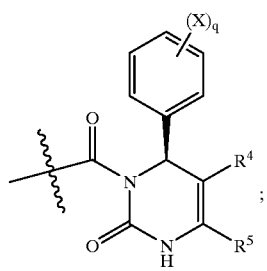

for example:

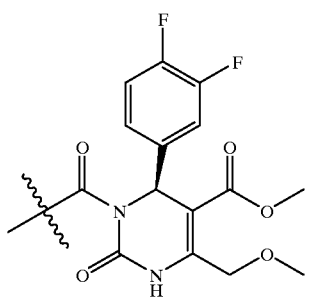

The term "activated (+)-DHP," as used herein, refers to a N-3-(activated)carbamate of the desired dihydropyrimidinone where the activated group is, for example, a p-nitrophenyl group. A specific example of an activated (+)-DHP is the compound 6 (see, e.g., Scheme 3).

The term "(S)-oxa" as used herein, refers to an oxazolidinone group of the formula

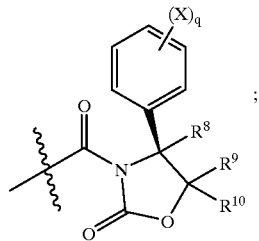

for example,

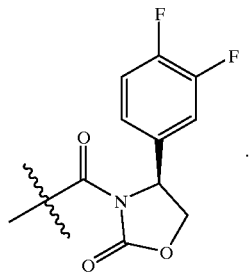

The term "activated (S)-oxa" as used herein, refers to an N-(activated)carbamate of the desired oxazolidinone where the activated group is, for example, a p-nitrophenyl group. A specific example of an activated (S)-oxa group is the compound 13 (see, e.g., Scheme 4).

The term "thienyl," as used herein, refers to the group

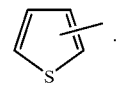

The term "selective alpha 1a adrenergic receptor antagonist," as used herein, refers to an alpha 1a antagonist compound which is at least ten fold selective for the human alpha 1a adrenergic receptor as compared to the human alpha 1b, alpha 1d, alpha 2a, alpha 2b and alpha 2c adrenergic receptors.

The term "lower urinary tract tissue," as used herein, refers to and includes, but is not limited to, prostatic smooth muscle, the prostatic capsule, the urethra and the bladder neck.

The term "subject," as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

As used herein, the term "composition" is intended to encompass a product comprising the specified ingredients in the specified amounts, as well as any product which results, directly or indirectly, from combination of the specified ingredients in the specified amounts.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Where the processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis,* John Wiley & Sons, 1991. The protecting groups may be removed at a convenient subsequent stage using methods known from the art.

The specificity of binding of compounds showing affinity for the alpha 1a receptor is shown by comparing affinity to membranes obtained from tranfected cell lines that express the alpha 1a receptor and membranes from cell lines or tissues known to express other types of alpha (e.g., alpha 1d, alpha 1b) or beta adrenergic receptors. Expression of the cloned human alpha 1d, alpha 1b, and alpha 1a receptors and comparison of their binding properties with known selective antagonists provides a rational way for selection of compounds and discovery of new compounds with predictable pharmacological activities. Antagonism by these compounds of the human alpha 1a adrenergic receptor subtype may be functionally demonstrated in anesthetized animals. These compounds may be used to increase urine flow without exhibiting hypotensive effects.

The ability of compounds of the present invention to specifically bind to the alpha 1a receptor makes them useful for the treatment of BPH. The specificity of binding of compounds showing affinity for the alpha 1a receptor is compared against the binding affinities to other types of alpha or beta adrenergic receptors. The human alpha adrenergic receptor of the 1a subtype was recently identified, cloned and expressed as described in PCT International Application Publication Nos. WO94/08040, published Apr. 14, 1994 and WO 94/21660, published Sep. 29, 1994. The cloned human alpha 1a receptor, when expressed in mammalian cell lines, is used to discover ligands that bind to the receptor and alter its finction. Expression of the cloned human alpha 1d, alpha 1b, and alpha 1a receptors and comparison of their binding properties with known selective antagonists provides a rational way for selection of compounds and discovery of new compounds with predictable pharmacological activities.

Compounds of this invention exhibiting human alpha 1a adrenergic receptor antagonism may further be defined by counterscreening. This is accomplished according to methods known in the art using other receptors responsible for mediating diverse biological functions. [See e.g., PCT International Application Publication No. WO94/10989, published May 26, 1994; U.S. Pat. No. 5,403,847, issued Apr. 4, 1995]. Compounds which are both selective amongst the various human alpha1 adrenergic receptor subtypes and which have low affinity for other receptors, such as the alpha2 adrenergic receptors, the β-adrenergic receptors, the muscarinic receptors, the serotonin receptors, and others are particularly preferred. The absence of these non-specific activities may be confirmed by using cloned and expressed receptors in an analogous fashion to the method disclosed herein for identifying compounds which have high affinity for the various human alpha1 adrenergic receptors. Furthermore, functional biological tests are used to confirm the effects of identified compounds as alpha 1a adrenergic receptor antagonists.

The present invention also has the objective of providing suitable topical, oral, systemic and parenteral pharmaceutical formulations for use in the novel methods of treatment of the present invention. The compositions containing compounds of this invention as the active ingredient for use in the specific antagonism of human alpha 1a adrenergic receptors can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an alpha 1a antagonistic agent.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacryl- amidephenol, polyhydroxy-ethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

Compounds of this invention may be administered in any of the foregoing compositions and according to dosage regimens established in the art whenever specific blockade of the human alpha 1a adrenergic receptor is required.

The daily dosage of the products may be varied over a wide range from 0.01 to 1,000 mg per adult human per day. For oral administration, the compositions are preferably provided in the form of tablets containing 0.01, 0.05, 0.1, 0.5, 1.0, 2.5, 5.0, 10.0, 15.0, 25.0, 50.0 and 100 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. An effective amount of the drug is ordinarily supplied at a dosage level of from about 0.0002 mg/kg to about 25 mg/kg of body weight per day. Preferably, the range is from about 0.001 to 10 mg/kg of body weight per day, and especially from about 0.001 mg/kg to 7 mg/kg of body weight per day. The compounds may be administered on a regimen of 1 to 4 times per day.

Compounds of this patent disclosure may be used alone at appropriate dosages defined by routine testing in order to obtain optimal antagonism of the human alpha 1a adrenergic receptor while minimizing any potential toxicity. In addition, co-administration or sequential administration of other agents which alleviate the effects of BPH is desirable. Thus, in one embodiment, this includes administration of compounds of this invention and a human testosterone 5-a reductase inhibitor. Included with this embodiment are inhibitors of 5-alpha reductase isoenzyme 2. Many such compounds are now well known in the art and include such compounds as PROSCAR®, (also known as finasteride, a 4-Aza-steroid; see U.S. Pat. Nos. 4,377,584 and 4,760,071, for example). In addition to PROSCAR®, which is principally active in prostatic tissue due to its selectivity for human 5-a reductase isozyme 2, combinations of compounds which are specifically active in inhibiting testosterone 5-alpha reductase isozyme 1 and compounds which act as dual inhibitors of both isozymes 1 and 2, are useful in combination with compounds of this invention. Compounds that are active as 5a-reductase inhibitors have been described in WO93/23420, EP 0572166; WO 93/23050; WO93/23038,; WO93/23048; WO93/23041; WO93/23040; WO93/23039; WO93/23376; WO93/23419, EP 0572165; WO93/23051.

The dosages of the alpha 1a adrenergic receptor and testosterone 5-alpha reductase inhibitors are adjusted when combined to achieve desired effects. As those skilled in the art will appreciate, dosages of the 5-alpha reductase inhibitor and the alpha 1a adrenergic receptor antagonist may be independently optimized and combined to achieve a synergistic result wherein the pathology is reduced more than it would be if either agent were used alone. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

Thus, in one preferred embodiment of the present invention, a method of treating BPH is provided which comprises administering to a subject in need of treatment any of the compounds of the present invention in combination with finasteride effective to treat BPH. The dosage of finasteride administered to the subject is about 0.01 mg per subject per day to about 50 mg per subject per day in combination with an alpha 1a antagonist. Preferably, the dosage of finasteride in the combination is about 0.2 mg per subject per day to about 10 mg per subject per day, more preferably, about 1 to about 7 mg per subject to day, most preferably, about 5 mg per subject per day.

For the treatment of benign prostatic hyperplasia, compounds of this invention exhibiting alpha 1a adrenergic receptor blockade can be combined with a therapeutically effective amount of a 5a-reductase 2 inhibitor, such as finasteride, in addition to a 5a-reductase 1 inhibitor, such as 4,7β-dimethyl-4-aza-5a-cholestan-3-one, in a single oral, systemic, or parenteral pharmaceutical dosage formulation. Alternatively, a combined therapy can be employed wherein the alpha 1a adrenergic receptor antagonist and the 5a-reductase 1 or 2 inhibitor are administered in separate oral, systemic, or parenteral dosage formulations. See, e.g., U.S. Pat. Nos. 4,377,584 and 4,760,071 which describe dosages and formulations for 5a-reductase inhibitors.

Abbreviations used in the instant specification, particularly the Schemes and Examples, are as follows:

AcOH or HOAc=acetic acid
BCE=bromochloroethane
BINAP=2,2'-bis(diphenylphosphino)-1,1'-binaphthyl
Bn=benzyl
Boc or BOC=t-butyloxycarbonyl
BOPCl=bis(2-oxo-3-oxazolidinyl)phosphinic chloride
Cbz-Cl=benzyloxycarbonyl chloride
dba=dibenzylideneacetone
DEAD=diethylazodicarboxylate
DIBAL=diisobutylalurminum hydride
DMF=N,N-dimethylformamide
DMSO=dimethylsulfoxide
EDCI=1-(3-dimethylaminopropyl)-3-ethylcarbodimide hydrochloride
Et=ethyl
Et$_3$N=triethylamine
EtOAc=ethyl acetate
EtOH=ethanol
FABLRMS=fast atom bombardment low resolution mass spectroscopy
HPLC=high performance liquid chromatography
HOAc=acetic acid
HOBt=1-hydroxy benzotriazole hydrate
i-PrOH=2-propanol
i-Pr2NEt=diisopropylethylamine
LAH=lithium aluminum hydride
mCPBA=meta-chloroperbenzoic acid
Me=methyl
MeOH=methanol
NMR=nuclear magnetic resonance
PCTLC=preparative centrifugal thin layer chromatography
PEI=polyethylenimine
Ph=phenyl
RT=retention time
tBu=tertiary butyl
TEBAC=benzyltriethylammonium chloride
TFA=trifluoroacetic acid
THF=tetrahydrofuran
TLC=thin layer chromatography
TMS=trimethylsilyl The compounds of the present invention can be prepared readily according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Unless otherwise indicated, all variables are as defined above.

The preparation of key intermediates for the compounds of the present invention was accomplished via either Pd mediated coupling reactions or direct nucleophilic displacement as outlined in Schemes 1 and 2. The products, for instance, 4-(ketalized) oxo or 4-hydroxy piperidines were converted to their corresponding piperidone derivatives either by acid catalyzed deketalization or Swern oxidation, respectively. The resulting ketones are further elaborated, for instance, via enolate alkylation. Once the desired ketones were in hand, reductive amination with the desired mono-blocked (protected) diamine was carried out by reaction with acetic acid in methanol followed by slow addition of a THF solution of sodium cyanoborohydride. On occasion, the newly generated secondary amine was protected or alkylated, the terminal amine deprotected and then coupled to the desired Q group via alkylation, acylation, reductive amination, etc.

The activated termini species comprising the "Q" groups are readily prepared by one of ordinary skill in the art. For example, oxazolidinones are prepared and activated in general by published and well developed chemistry, in particular, of Evans. [Evans, D. A.; Nelson, J. V.; Taber, R. R. Top. Stereochem. 13, 1 (1982)] The starting materials, in general, are natural and unnatural amino acids. For instance, some of the preferred compounds are prepared from substituted phenylglycine derivatives, which after reduction of the carboxylate and a phosgene equivalent mediated cyclization provides the substituted oxazolidinone ring system. Deprotonation with n-butyl lithium and addition to a THF solution of p-nitrophenylchloroformate produces the stable, isolable "activated" oxazolidinone (oxa).

Dihydropyrimidinones are prepared by condensation reaction of the aldehyde, urea and 1,3-acetoacetate type derivative catalyzed by a Lewis Acid, a copper (I) species and acetic acid. Activation was accomplished by treatment with a strong base, for instance, LiN(TMS)$_2$, followed by addition to a THF solution of p-nitrophenylchloroformate.

Hydantoins and cycloimide were prepared in two chemical steps from ketones as outlined in the literature. More specifically, hydantoins were prepared according to known methodology, e.g., J. J. Edmunds et al., *J. Med. Chem.* 1995, 38, pp. 3759–3771; J. H. Poupart et al., *J. Chem. Res.* 1979, pp. 174–175. Saccharins were prepared according to known methods, e.g., page 40 and Examples 21 and 22 of PCT International Application Publication No. WO96/25934, published Aug. 29, 1996.

The dihydropyrimidinones and oxazolidinones were synthesized independently in racemic form, and then separated utilizing preparative chiral HPLC. Their optical rotations were recorded. Then they were activated and reacted with prerequisite amines. From the receptor binding studies, a preferred isomer was identified, the (+) rotational isomer in each case. The absolute configurations were determined to be (S) for both the dihydropyrimidinones and oxazolidinones by correlating their optical rotations with x-ray crystal structures obtained of fragments involved in the production of the antagonists.

Examples of the preparation of some desired compounds are outlined in Schemes 3–5. Selective Boc protection of 4-amino methylpiperidine (1) followed by reductive amination with ketone (3) provided the terminally protected amino derivative (4). Acid mediated deprotection of (4) followed by acylation with (6) and (22) provided (7) and (23), Scheme 3 and 4.

Other derivatives were prepared via the routes outlined in Schemes 5–7. For example, N-protected 3-hydroxy azetidine (8) was tosylated providing (9). Displacement with sodium azide produced (10) which after reduction with $PPH_3/H2O$ resulted in N-protected-3-aminoazetidine (11). Reductive amination with ketone (3) produced (12) which after Boc protection of the secondary amine, hydrogenolysis of the N-protecting group, acylation and HCl/EtOAc mediated concomitant deprotection and salt formation yields the desired products.

Still other derivatives were prepared via the routes outlined in Schemes 8 and 9. The synthesis of the 3-aminomethylpyrrolidine intermediate was accomplished from the commercially available lactam as outlined Scheme 8. The ester was converted to the amide by a simple two step process. Subsequent DIBAL reduction yielded the monoprotected diamino intermediate. Reductive aminations with cyclohexanones, followed by deprotection of the N-benzyl group, and acylation with preferred activated "Q"-groups furnished the final targets.

The synthesis of the 4-amino-3-hydroxypyrrolidine intermediate began with 3,4-pyrroline, Scheme 9. BOC protection of the amine followed by mCPBA oxidation provided the epoxidation. Subsequent sodium azide opening of the epoxide and triphenylphosphine/water mediated reduction produced 4-amino-N-1-(1,1-dimethylethoxycarbonyl)-3-hydroxypyrrolidine. The key amino intermediate was alkylated by reductive amination reactions with cyclohexanones. Following the cleavage of the BOC protecting group acyclation with preferred activated "Q"-groups furnished the final targets.

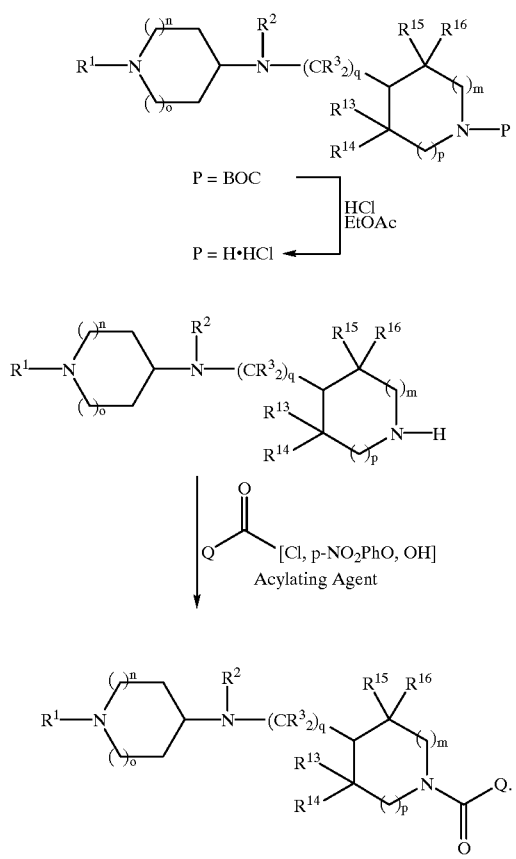

SCHEME 1

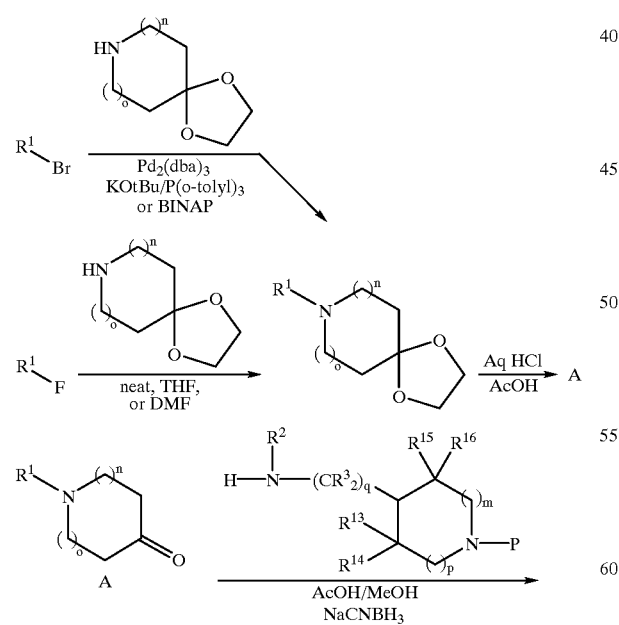

SCHEME 2

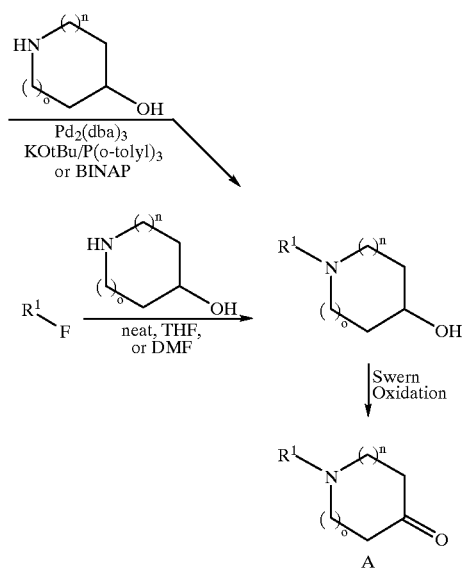

SCHEME 3
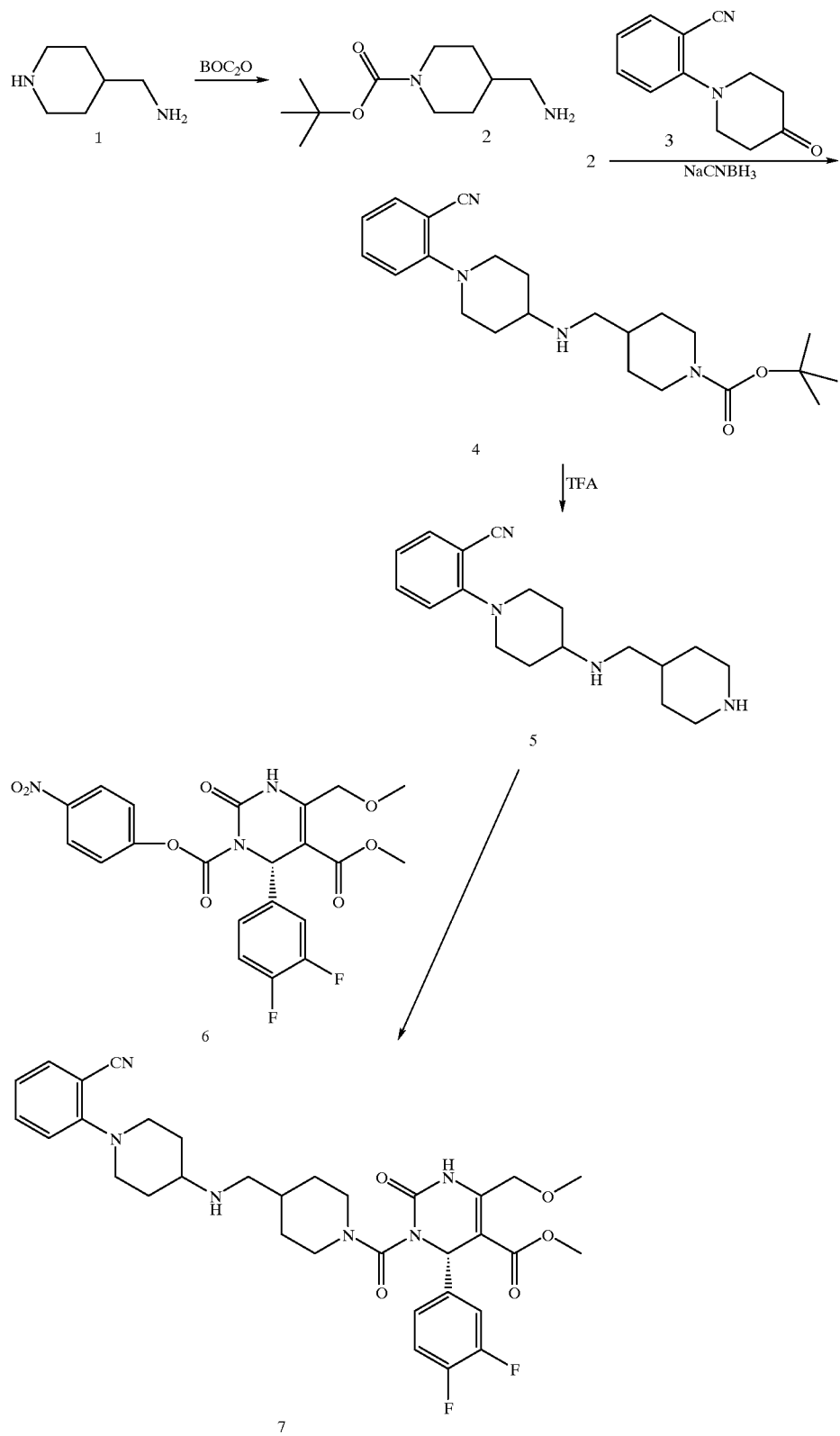

SCHEME 4
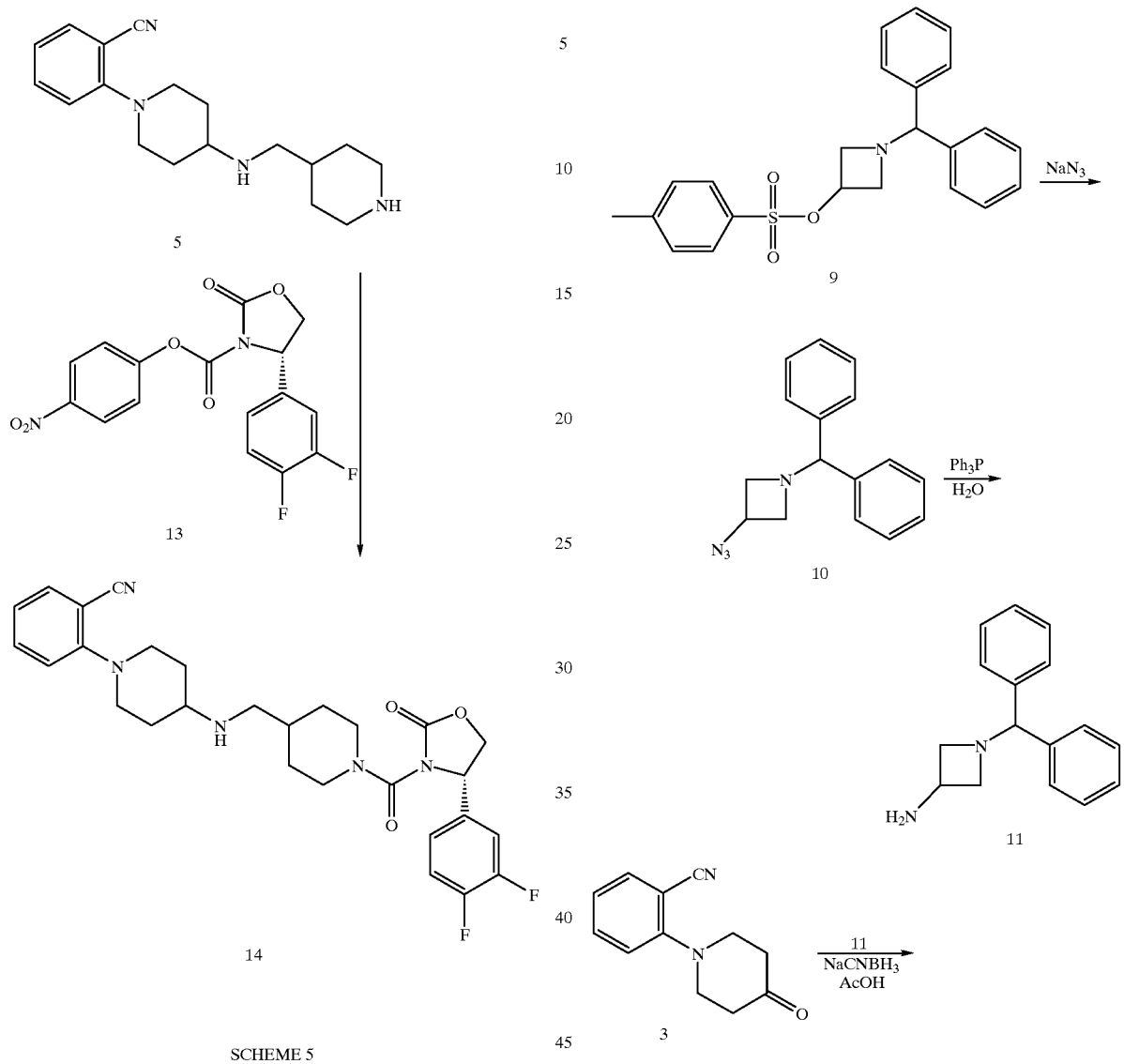
SCHEME 5
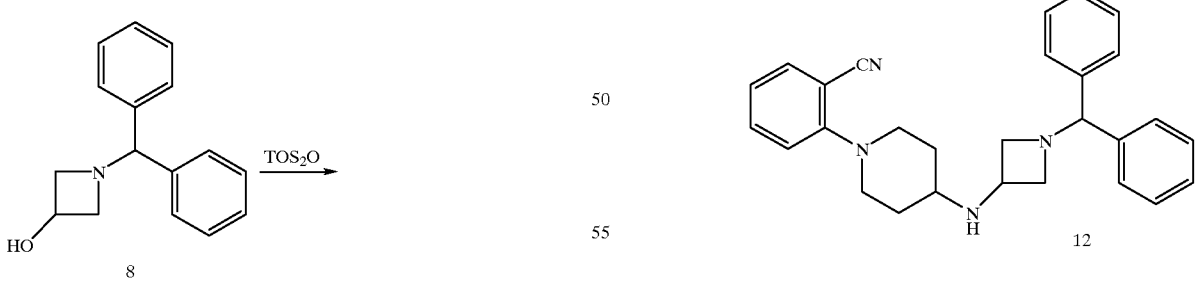

SCHEME 6
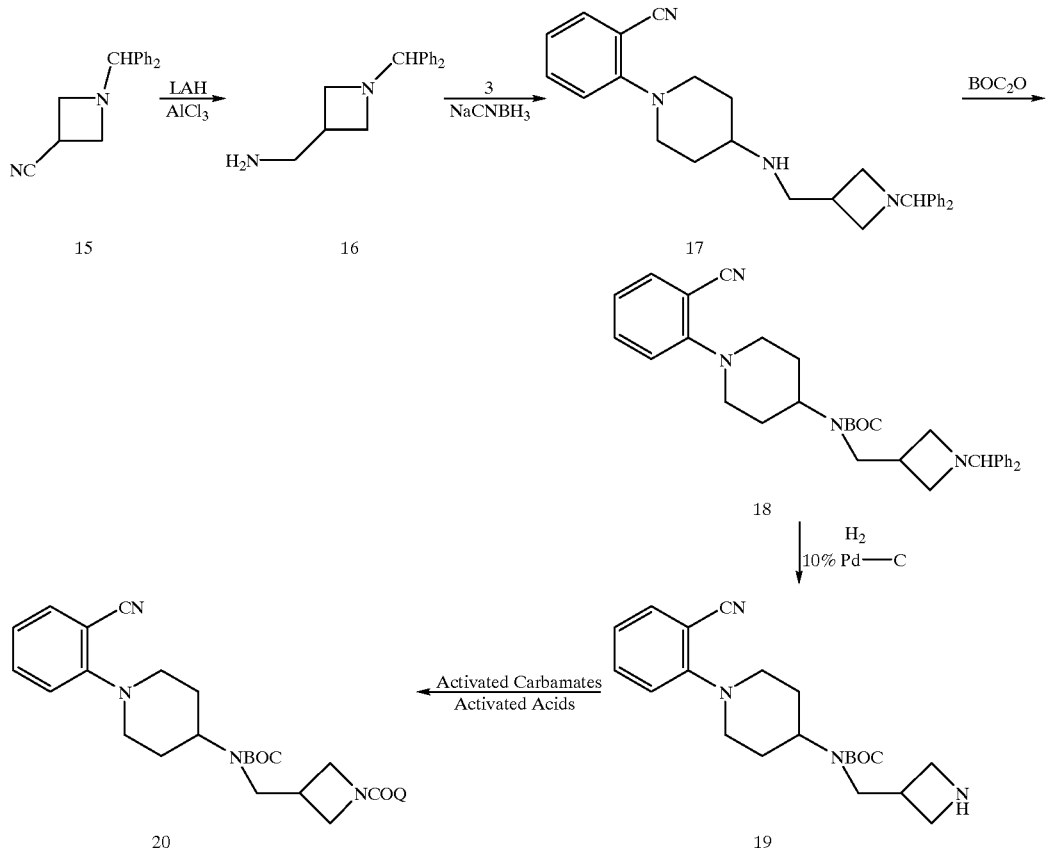
SCHEME 7
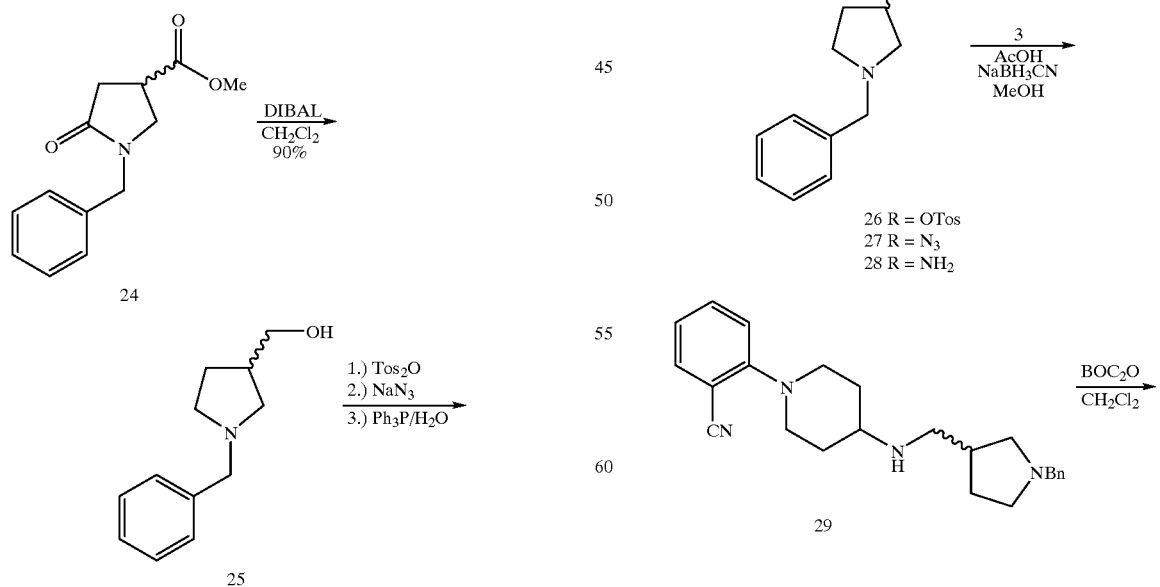

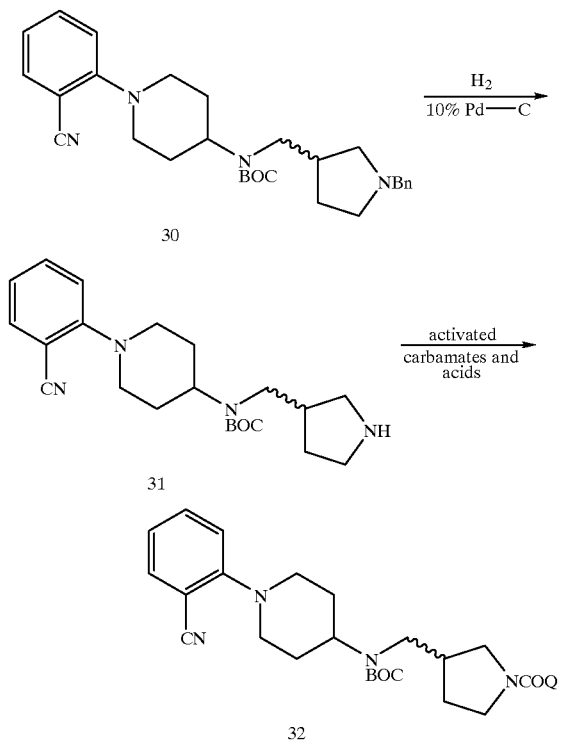

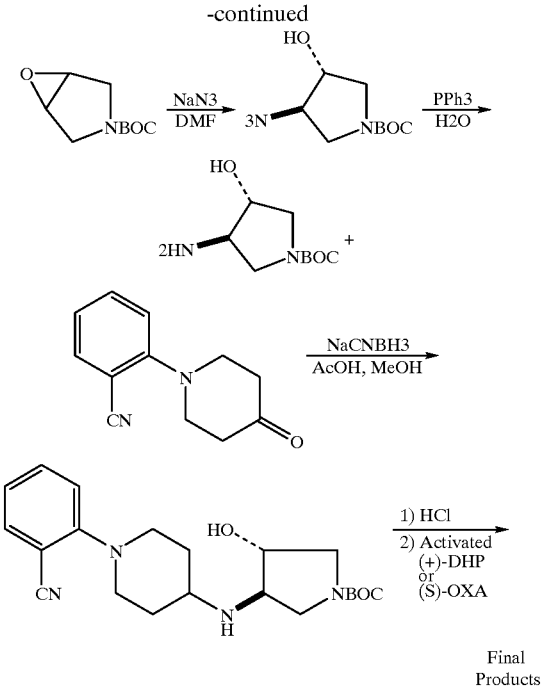

The following examples are provided to further define the invention without, however, limiting the invention to the particulars of these examples.

EXAMPLE 1

4-Aminomethyl-piperidine-1-carboxylic acid tert-butyl ester (2)

A solution of C-piperidin-4-yl-methylamine (1) (5.0 g, 44 mmol) and triethylamine (12 ml 88 mmol) in 150 ml of chloroform was cooled to 0° C. To this solution was added dropwise ditertbutyldicarbonate (8.6 g, 40 mmol) in 100 ml of chloroform. After stirring at room temperature for 24 hours the solution was washed with water, dried over MgSO$_4$, filtered and the solvents removed in vacuo to give the title compound $^1$H NMR (CDCl$_3$) 4.20–4.00 (br m, 2H), 2.75–2.62 (br t, 2H), 2.60 (d, 2H), 1.75–1.65 (br m, 2H), 1.50–1.30 (m, 3H), 1.63 (s, 9H), 1.20–1.00 (m, 2H).

EXAMPLE 2

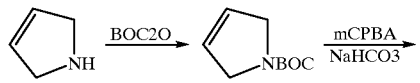

N-(2-cyanophenyl)-4-pipieridone (3)

A solution of 2-fluorobenzonitrile (2.75 g, 22.7 mmol) and 4-piperidone ethylene ketal (4.25 g, 29.7 inmol) in DMF (40 mL) was heated to 120° C. for 4h. The resulting mixture was cooled to room temperature overnight. The solvent was removed in vucuo and the residue dissolved in ether and sodium bicarbonate solution. The aqueous layer was extracted with two additional portions of ether and the combined organic extracts were washed with brine, dried over Na$_2$SO$_4$, and concentrated under reduced pressure to afford the 4-piperidone ethylene ketal. The crude product was used directly.

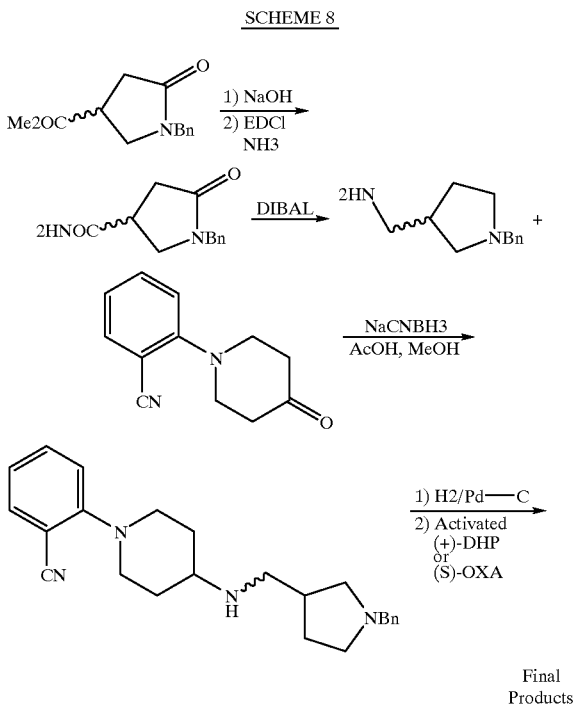

A solution of 4-piperidone ethylene ketal (533 mg, 2.18 mmol) in ether (10 mL) was treated with 5% aqueous HCl (20 mL). The mixture was stirred at room temperature (11d). The reaction was diluted with ether and neutralized with sodium bicarbonate solution. The aqueous layer was extracted with two additional portions of ether and the combined organic extracts were washed with brine, dried over $Na_2SO_4$, and concentrated under reduced pressure. PCTLC ($SiO_2$, 4 mm, 20% EtOAc; 80% hexane) afforded the title compound (3).

$^1$H NMR ($CDCl_3$, 400 MHz) consistant with assigned structure.

FABLRMS m/e 201 g/mole ($M^+{}_+H$, $C_{12}$ $H_{12}$ $N_2O$=201 g/mole.)

HPLC (Vydac; C18; diameter=4.6 mm; length=150 mm; gradient=$H_2O$ [0.1% $H_3PO_4$] —$CH_3CN$, 95%–5%, 5%–95%, over 16 minutes, 2 ml/min flow rate) RT=7.32 min; focus=215 nm; 97.5% pure.

EXAMPLE 3
4-{[1-(2-Cyano-phenyl)-piperidin-4-ylamino]-methyl}-cyclohexanecarboxylic acid tert-butyl ester (4)

To a solution of 2-(4-oxo-piperidin-1-yl)-benzonitrile (3) (750 mg, 3.75 mmol) and 2 in 40 ml of methanol was added 4 g of powdered 4 Å molecular sieves. The resulting suspension was stirred at room temperature for 24 hours. The suspension was subsequently acidified to pH 5 with acetic acid and a 1M solution of $NaCNBH_3$ in THF (6.0 ml 5.6 mmol) was added slowly with a syringe pump over 24 hours. When the addition was complete, the solvent was removed in vacuo and the residue taken up in chloroform and filtered. The solution was then washed with 10% $Na_2CO_3$, dried over $MgSO_4$, and the solvent removed in vacuo to give the crude amine. The crude product was purified by chromatography on silica gel (5% MeOH/$CHCl_3$) to give the title compound.

$^1$H NMR ($CDCl_3$) 7.54 (dd, 1H, J=7.56 Hz,1.46 Hz), 7.45, (t, 1H, J=7.94 Hz), 7.01–6.94 (m, 2H), 4.18–4.05, (m, 2H), 3.61–3.52 (m, 2H), 2.81–2.95 (m, 2H), 2.78–2.57 (m, 3H), 2.55 (d, 2H, J=6.59 Hz), 2.09–1.95 (m, 2H), 1.72 (br d, 2H, J=12.7 Hz), 1.70–1.50 (m, 3H), 1.45 (s, 9H), 1.45–1.30, (m, 1H), 1.20–1.00 (m, 2H).

EXAMPLE 4
2-{4-[(Piperidin-4-ylmethyl)-amino]-piperidin-1-yl}-benzonitrile (5)

To a solution of 4 (1.5 g, 3.76 mmol) in 30 ml of methylene chloride was added 15 ml of TFA. After stirring at room temperature for 24 hours, the solvents were removed in vacuo and the residue partitioned between chloroform and 10% $Na_2CO_3$. The organics were dried over $MgSO_4$, filtered, and the solvent removed in vacuo to give the title compound.

$^1$H NMR ($CDCl_3$) 7.54 (dd, 1H, J=7.57 Hz, J=1.47 Hz), 7.50–7.40 (m, 1H), 7.03–6.95, (m, 2H), 3.61–3.55 (m, 2H), 3.30–3.20 (m, 2H), 2.87 (d of t, 2H, J=12.45 Hz, J=2.44 Hz), 2.74 (d of t, 2H, J=12.45Hz, J=2.68 Hz), 2.63–2.55 (m, 1H), 2.57 (d, 2H, J=6.83), 2.08–1.97 (m, 2H), 1.95–1.83 (m, 2H), 1.67–1.50 (m, 3H), 1.42–1.25 (m, 2H).

EXAMPLE 5
3-(4-{[1-(2-Cyano-phenyl)-piperidin-4-ylamino]-methyl}-piperidine-1-carbonyl)-4-(3,4-difluoro-phenyl)-6-methoxymethyl-2-oxo-1,2,3,4-tetrahydro-pyrimidine-5-carboxylic acid methyl ester (7)

To a solution of 5 (280 mg, 0.94 mmol) in 30 ml of chloroform was added dropwise 6 in 10 ml of chloroform. The resulting solution was stirred for 20 minutes and the crude material purified by chromatography on silica gel (5% MeOH/$CHCl_3$)

$^1$H NMR (DMSO-$d_6$ 75° C.) 7.63 (d, 1H, J=7.57 Hz), 7.55 (t, 1H, J=7.57 Hz), 7.42–7.25 (m, 2H), 7.13 (d, 2H, J=8.31 Hz), 7.03 (t, 1H, J=7.57 Hz), 5.67 (s, 1H), 4.51 (AB q, 2H Ja=48.1 Hz, Jb=13.43Hz, 3.90–3.50 (m, 2H), 3.60 (s, 3H), 3.45 (d, 2H J=11.96Hz), 3.31 (s, 3H), 2.90–2.65 (m, 4H), 2.60–2.45 (m, 1H), 2.39 (d, 2H J=5.86Hz), 1.90 (d, 2H, J=10.74Hz)1.75–1.35 (m, 8H), 1.05–0.90 (m, 1H).

MS (FAB) 637 (M+1)

Analysis calculated for $C_{33}$ $H_{38}$ $N_6O_5F_2$ 0.50 $CHCl_3$, 0.25 $H_2O$: C, 57.40; H, 5.61; N, 11.99. Found: C, 57.40; H, 5.56; N, 12.18.

EXAMPLE 6
Toluene-4-sulfonic acid 1-benzhydryl-azetidin-3-yl ester (9)

To a cooled (0° C.) solution of 8 (7 g, 29 mmol) in 100 ml of chloroform was added paratoluene sulfonic anhydride (11.5 g, 35.2mmol), and triethylamine (12 ml, 88mmol). The resulting solution was stirred at room temperature for 24 hours. The solution was subsequently washed with water, dried over $MgSO_4$, filtered, and the solvent removed in vacuo. The crude material was purified by chromatography on silica gel to give the desired product as an oil.

$^1$H NMR ($CDCl_3$) 7.75 (d, 2H, J=8.3Hz), 7.35–7.15 (m, 12H), 4.95–4.82 (m, 1H), 4.32 (s, 1H), 3.50–3.40 (m, 2H), 3.10–3.00 (m, 2H), 2.43 (s, 3H).

EXAMPLE 7
3-Azido-1-benzhydryl-azetidine (10)

A solution of 9 (11.5 g, 31.8 mmol) and sodium azide (4.12 g, 64 mmol) in 250 ml of DMF was heated to 70° C. for 24 hours. After cooling to room temperature the solvent was removed in vacuo and the residue partitioned between chloroform and water. The organics were dried over $MgSO_4$, filtered and the solvent removed in vacuo. The crude product was purified by chromatography on silica gel (8:1 hexane: ethyl acetate) afforded the title compound.

$^1$H NMR ($CDCl_3$) 7.41–7.15 (m, 10H), 4.33 (s, 1H), 4.02–3.95 (m, 1H) 3.50–3.41 (m, 2H), 3.07–3.00 (m, 2H).

EXAMPLE 8
1-Benzhydryl-azetidin-3-ylamine (11)

A solution of 10 (5.7 g, 21.6 mmol), triphenylphosphine (11.3 g, 43 mmol) and water (5 ml) was heated to reflux for 24 hours. After cooling to room temperature the solvent was removed in vacuo and the residue purified by chromatography on silica gel (90:9:1 $CHCl_3$:MeOH:$NH_4OH$).

$^1$H NMR ($CDCl_3$) 7.41–7.15 (m, 10H), 4.27 (s, 1H), 3.65–3.55 (m, 1H), 3.55–3.50 (m, 2H), 2.65–2.60 (m, 2H) 1.44 (br s, 2H).

EXAMPLE 9
2-[4-(1-Benzhydryl-azetidin-3-ylamino)-piperidin-1-yl]-benzonitrile trifluoroacetic acid salt (12)

The title compound was prepared from 3 (1.0 g, 3.9 mmol) and 11 using the procedure described for 4.

$^1$H NMR ($CDCl_3$) 7.56–6.90 (m, 14H), 4.32 (s, 1H), 3.62–3.45 (m, 5H), 2.90–2.87 (m, 2H), 2.75–7.65 (m, 2H), 2.64–2.58 (m, 1H), 1.91 (d, 2H, J=11.36Hz), 1.62–1.53 (m, 2H), 1.50–1.20 (br s, 1H).

MS (FAB) 423 (M+1).

Analysis calculated for $C_{28}$ $H_{30}$ $N_4$ 0.05 $H_2O$, 2.30 TFA: C, 57.10; H, 4.76; N, 8.17. Found: C, 57.10; H, 4.75; N, 8.25.

EXAMPLE 10
2-[4-({1-[4-(3,4-Difluoro-phenyl)-2-oxo-oxazolidine-3-carbonyl]-piperidin-4-ylmethyl}-amino)-piperidin-1-yl]-benzonitrile trifluoroacetic acid salt (14)

The title compound was prepared from 5 (200 mg, 0.67 mmol) and 13 (121 mg, 0.67 mmol) using the procedure described for 7.

¹H NMR (CD₃OD) 7.70–7.55 (m, 2H), 7.50–7.40 (m, 1H), 7.35–7.25 (m, 2H) 7.20–7.03 (m, 2H), 5.50 (t, 1H, J=9.03Hz), 4.75 (t, 1H, J=8.54Hz), 4.30–4.13 (m, 3H), 3.65 (d, 2H, J=12.21 Hz), 3.15–2.85 (m, 6H), 2.25 (d, 2H, J=10.26Hz), 2.10–1.75 (m, 6H), 1.50–1.10 (m, 2H).

MS (FAB) 524 (M+1).

Analysis calculated for $C_{28} H_{31} N_5 O_3 F_2$ 1.30 TFA, 0.20 $H_2O$: C, 54.41; H, 4.88; N, 10.37. Found: C, 54.37; H, 4.88; N, 10.46.

EXAMPLE 11

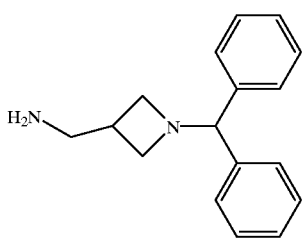

3-Aminomethyl N-diphenylmethyl azetidine, (16)

To a cooled solution of aluminum chloride (0.33 g, 2.41 mmol) in ether (50 mL) at −78° C. was added lithium aluminum hydride (2.41 ml, 2.41 mmol). After stirring 15 minutes at −78° C. the slurry was added a solution of 15 (0.50 g, 2.01 mmol) in ether (10 mL) dropwise. The resulting mixture was stirred at room temperature for 2 hours. The solution was cooled to 0° C. and quenched with water (10 mL) dropwise followed by 25% NaOH solution (10 mL). The aqueous layer was extracted with EtOAc. The organics were dried over $Na_2SO_4$, filtered, and removed in vacuo. The crude product was not purified.

¹H NMR (CDCl₃, 300 MHz) 7.41–7.13 (m, 10H), 4.32 (s, 1H), 3.28 (t, 2H), 2.88–2.79 (m, 4H), 2.52–2.42(m, 1H), 1.28 (s, 1H).

EXAMPLE 12

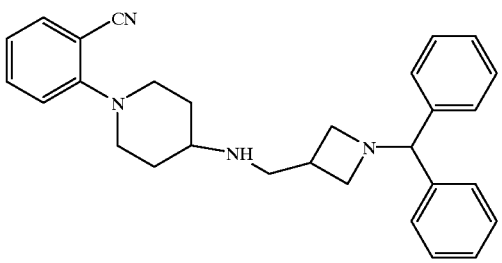

Compound (17)

The title compound was prepared from 16 and 3 using the procedure described for the preparation of 4.

¹H NMR (CDCl₃, 400 MHz) 7.54–7.51 (dd, 1H), 7.46–7.38 (m, 5H), 7.28–7.24 (m, 4H), 7.18–7.15 (m, 2H), 6.99–6.93 (m, 2H), 4.33 (s, 1H), 3.57–3.45 (m, 2H), 3.35–3.31 (t, 2H), 2.89–2.79 (m, 7H), 2.64–2.56 (m, 2H), 2.01–1.98 (m, 2H), 1.62–1.53 (m, 2H).

MS (FAB) 437 (M+1).

EXAMPLE 13

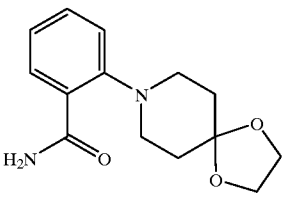

N-(2-benzamido)-4-piperidone ethylene ketal (21)

A mixture of 2-fluorobenzamide (7.0 g, 50.0 mmol) and 4-piperidone ethylene ketal (7.16 g, 50.0 minol) was heated at 100° C. (7 d). The solvent was removed in vacuo and triturated with ether affording the title compound (21).

¹H NMR (DMSO-d₆, 300 MHz) consistant with assigned structure.

HPLC (Vydac; C18; diameter=4.6 mm; length=150 mm; gradient=H₂O [0.1% H₃PO₄] —CH₃CN, 95%–5%, 5%–95%, over 16 minutes, 2 ml/min flow rate) RT=4.49 min; focus=215 nm; 100% pure.

EXAMPLE 14

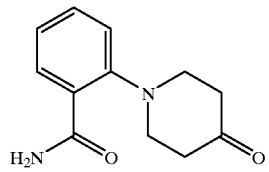

N-(2-benzamido)-4-piperidone (22)

A solution of the ketal 21 (13.2 mg, 46.753 mmol) in acetic acid (50 mL) and 6N aqueous HCl (50 mL) was heated at 60° C. (12 h), 80% conversion. The solvent was removed in vacuo, neutralized with 25% aqueous NaOH, extracted with CHCl₃ (3×250 mL), the combined organic extracts were washed with brine, dried over $Na_2SO_4$, and concentrated under reduced pressure to give (22) which was used without further purification.

¹H NMR (CDCl₃, 400 MHz) consistant with assigned structure.

EXAMPLE 15

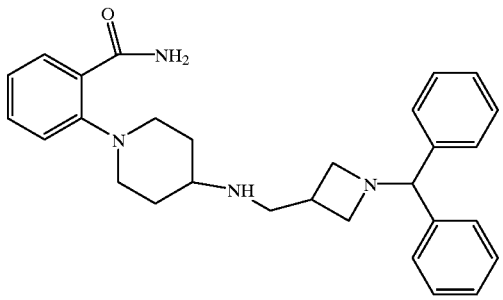

Compound (23)

The title compound was prepared from 16 and 22 using the procedure described for the preparation of 4.

¹H NMR (CDCl₃, 400 MHz) 9.53 (s, 1H), 8.16–8.13 (m, 1H), 7.45–7.38 (m, 6H), 7.29–7.21 (m, 2H), 7.19–7.15 (m, 4H), 5.76 (s, 1H), 5.29 (s, 1H), 4.33 (s, 1H), 3.36–3.32 (t, 2H), 3.20–3.17 (d, 2H), 2.87–2.75 (m, 7H), 2.64–2.55 (m, 2H), 2.03–2.00 (d, 2H), 1.55–1.45 (m, 2H).

EXAMPLE 16

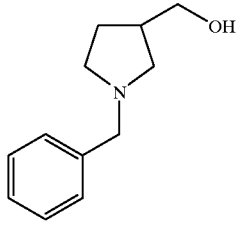

N-1-Benzyl-3-hydroxymethyl pyrrolidine (25)

A solution of Methyl 1-benzyl-5-oxo-3-pyrrolidinecarboxylate (24) (10.0 g, 42.8 mmol) in 175 ml of dichloromethane was added dropwise to a cooled solution of 1.5 M DIBAL-H (143 mL, 214 mmol) at −78° C. After stirring at room temperature for 48 hours the solution was cooled to 0° C. and added 25 mL methanol dropwise. The solution was added 250 mL saturated aqueous Rochelle salts and extracted with chloroform. The combined organics were dried over MgSO$_4$, filtered and the solvents removed in vacuo to give the crude alcohol. The crude product was purified by chromatography on silica gel (7% MeOH/CHCl$_3$) to afford the title compound.

$^1$H NMR (CDCl$_3$, 400 MHz) 7.33–7.24 (m, 5H), 3.70–3.66 (m, 1H), 3.59–3.48 (m, 4H), 2.86–2.80 (m, 1H), 2.66–2.63 (d, 1H), 2.51–2.47 (t, 1H), 2.34–2.28 (m, 2H), 2.05–1.96 (m, 1H), 1.75–1.67 (m, 1H).

EXAMPLE 17

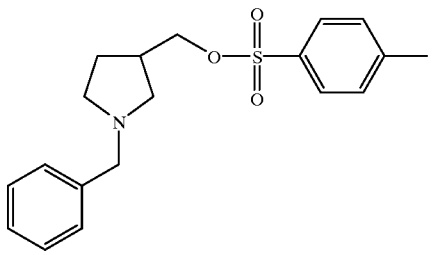

Toluene-4-sulfonic acid 1-benzyl-pyrrolidin-3-methyl ester (26)

To a cooled (0° C.) solution of 25 (1.0 g, 5.2 mmol) in 100 ml of chloroform was added para-toluenesulfonic anhydride (2.5 g, 7.8 mmol), and triethylamine (2.1 ml, 15 mmol). The resulting solution was stirred at room temperature for 24 hours. The solution was subsequently washed with water, dried over MgSO$_4$, filtered, and the solvent removed in vacuo. The crude material was purified by chromatography on silica gel to afford the desired product.

$^1$H NMR (CDCl$_3$, 400 MHz) 7.78–7.76 (d, 2H), 7.33–7.23 (m, 7H), 3.94–3.92 (m, 2H), 3.53 (s, 2H), 2.58–2.43 (m, 6H), 2.27–2.24 (m, 1H), 1.97–1.88 (m, 1H), 1.44–1.36 (m, 1H).

EXAMPLE 18

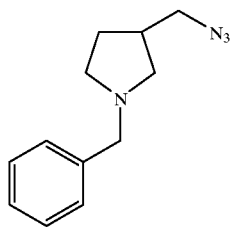

N-1-Benzyl-3-azidomethyl pyrrolidine (27)

A solution of 26 (1.26 g, 3.64 mmol) and sodium azide (0.474 g, 7.29 mmol) in 100 ml of DMF was heated to 70° C. for 24 hours. After cooling to room temperature the solvent was removed in vacuo and the residue partitioned between chloroform and water. The organics were dried over MgSO$_4$, filtered and the solvent removed in vacuo to afford the azide.

$^1$H NMR (CDCl$_3$, 400 MHz) 7.34–7.22 (m, 5H), 3.60–3.59 (d, 2H), 3.28–3.26 (m, 2H), 2.70–2.66 (m, 1H), 2.57–2.54 (t, 1H), 2.44–2.38 (m, 2H), 2.31–2.27 (m, 1H), 2.04–1.98 (m, 1H), 1.51–1.45 (m, 1H).

EXAMPLE 19

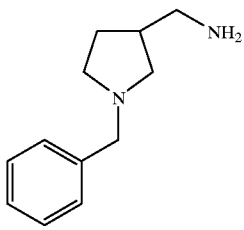

N-1-Benzyl-3-aminomethyl pyrrolidine (28)

A solution of 27 (0.71 g, 3.2 mmol), triphenylphosphine (1.7 g, 6.5 mmol), THF (50 mL), and water (5 mL) was heated to reflux for 24 hours. After cooling to room temperature the solvent was removed in vacuo and the residue purified by chromatography on silica gel (90:9:1 CHCl$_3$:MeOH:NH$_4$OH) to afford the amine.

$^1$H NMR (CDCl$_3$, 400 MHz) 7.33–7.22 (m, 5H), 3.60–3.58 (d, 2H), 2.76–2.72 (m, 1H), 2.60–2.58 (m, 3H), 2.52–2.47 (m, 1H), 2.24–2.17 (m, 2H), 2.00–1.95 (m, 1H), 1.48–1.42 (m, 1H), 1.12 (br s, 2H).

EXAMPLE 20

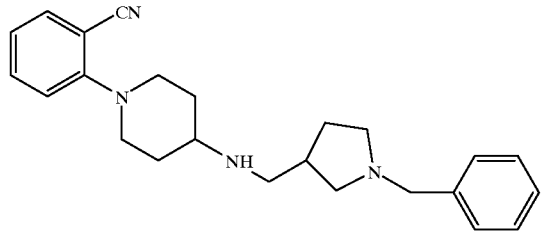

Compound (29)

The title compound was prepared from 28 and 3 using the procedure described for the preparation of 4.

$^1$H NMR (CDCl$_3$, 400 MHz) 7.54–7.52 (d, 1H), 7.46–7.42 (t, 1H), 7.33–7.22 (m, 5H), 6.99–6.93 (m, 2H),

Anal. Calcd for C$_{29}$H$_{34}$N$_4$O$_1$. 0.05 CHCl$_3$+0.60 H$_2$O: C=74.01, H=7.54, N=11.89. Found: C=74.06, H=7.51, N=11.57. MS (FAB) 455 (M+1)

3.65–3.48 (m, 6H), 3.89–2.83 (t, 2H), 2.79–2.74 (t, 1H), 2.66–2.59 (m, 4H), 2.55–2.49 (q, 1H), 2.34–2.28 (m, 1H), 2.23–2.19 (t, 1H), 2.01–1.98 (m, 3H), 1.63–1.52 (m, 2H), 1.50–1.45(m, 1H).

Anal. Calcd for $C_{24}H_{32}N_4Cl_2$. 0.25 Hcl+0.35 ETOAc: C=62.59, H=7.25, N=11.50. Found: C=62.60, H=7.10, N=11.46.

MS (FAB) 375 (M+1)

EXAMPLE 21

Mixture of 4S-4-(3,4-difluorophenyl)-6-methoxymethyl-2-oxo-1,2,3,4-tetrahydropyrimidine and 4S-4-(3,4-difluorophenyl)-6-methoxymethyl-2-oxo-2,3,4,5-tetrahydropyrimidine

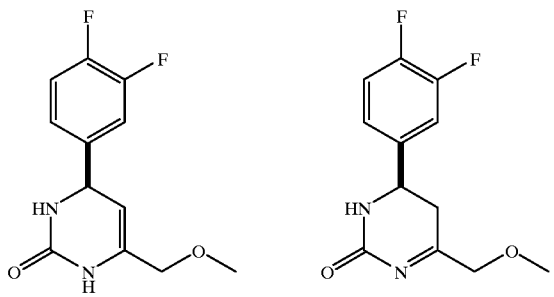

To a solution of (+)-4-(3,4-difluorophenyl)-6-methoxymethyl-2-oxo-1,2,3,4-tetrahydropyrimidine-5-carboxylic acid methyl ester (4.63 g, 14.7 mmol) in a methanol (100 ml) was added sodium hydroxide (2.94 g, 73.6 mmol). The resulting mixture was refluxed at 90° C. for 16 hours. After cooling to room temperature the solvent was removed in vacuo. The solid was dissolved in $CH_2Cl_2$ and $H_2O$ then neutralized with 10% aqueous HCl solution. The organic layer was dried over $Na_2SO_4$, concentrated, and purified by PCTLC (7% MeOH in $CHCl_3$ with 2% $NH_4OH$) to afford a 2.65 g mixture of the title compounds (71% yield). The $^1H$ NMR was consistent with the assigned structure.

MS (FAB) 255 (M+1)

EXAMPLE 22

Mixture of 4S-4-(3,4-difluorophenyl)-6-methoxymethyl-2-oxo-1,2,3,4-tetrahydropyrimidine and 4S-4-(3,4-difluorophenyl)-6-methoxymethyl-2-oxo-2,3,4,5-tetrahydropyrimidine

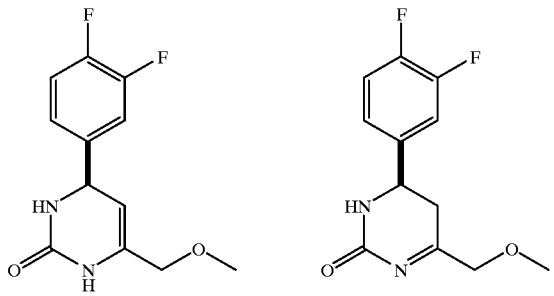

To a solution of (+)-4-(3,4-difluorophenyl)-6-methoxymethyl-2-oxo-1,2,3,4-tetrahydropyrimidine-5-carboxylic acid methyl ester (5.36 g, 17.0 mmol) in a methanol (150 ml) was added 1N NaOH (10 ml). The resulting mixture was refluxed at 90° C. for 16 hours. After cooling to room temperature the solvent was removed in vacuo. The solid was dissolved in $CH_2Cl_2$ and $H_2O$ then neutralized with 10% aqueous HCl solution. The organic layer was dried over $Na_2SO_4$, concentrated, and purified by PCTLC (7% MeOH in $CHCl_8$ with 2% $NH_4OH$) to afford a 2.35 g mixture of the title compounds (54% yield). The $^1H$ NMR was consistent with the assigned structure.

MS (FAB) 255 (M+1)

EXAMPLE 23

4S-4-(3,4-Difluorophenyl)-6-methoxymethyl-3-(4-nitrophenoxycarbonyl)-2-oxo-1,2,3,4-tetrahydropyrimidine-5-carboxylic acid methyl ester

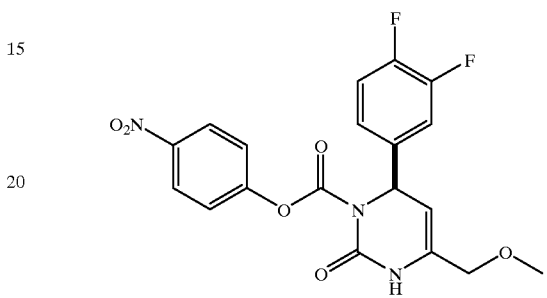

The title compound was prepared by treating the mixture obtained from Example 21 or Example 22 (1.93 g, 7.59 mmol) with lithium diisopropylamide (2.0 M THF solution, 1.1 equivalents) in THF at −78° C. for 20 minutes followed by the rapid addition of 4-nitrophenyl chloroformate (1.5 equivalents) in THF. 0.488 g of the title compound was obtained in a 15% yield. The $^1H$ NMR was consistent with the assigned structure.

EXAMPLE 24

Mixture of 4R-4-(3,4-difluorophenyl)-6-methoxymethyl-2-oxo-1,2,3,4-tetrahydropyrimidine and 4R-4-(3,4-difluorophenyl)-6-methoxymethyl-2-oxo-2,3,4,5-tetrahydropyrimidine

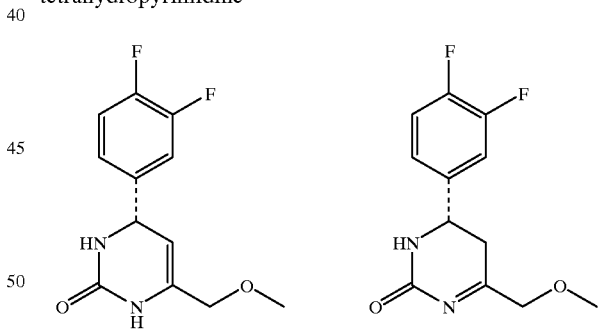

The title compounds were prepared from 4R-4-(3,4-difluorophenyl)-6-methoxymethyl-2-oxo-1,2,3,4-tetrahydropyrimidine-5-carboxylic acid methyl ester (5.0 g, 17.7 mmol) using the procedure described in Example 7. A mixture of 2.0 g of the title compounds was obtained in 50% yield. The $^1H$ NMR was consistent with the assigned structure.

MS (FAB) 255 (M+1)

Compounds of the invention can be prepared by reacting the products obtained in Example 23 in accordance with procedures and schemes described above. The compound of Example 23 can, for example, be acylated with an arylpiperidinyl aminoalkylpiperidine in accordance with Scheme 3 to obtain the desired compounds. Compounds of the invention can also be prepared by preparing a nitrophenoxy derivative of the compound of Example 24 in accordance with the procedure set forth in Example 23 and then reacting the derivative with an arylpiperidinyl aminoalkylpiperidine as set forth in Scheme 3 to obtain compounds of the invention.

Examples 25 and 26 were prepared as outlined in Scheme 8.

EXAMPLE 25
(4S)-2-[4-({1-[4-(3,4-Difluorophenyl)-2-oxo-oxazolidine-3-carbonyl]-pyrrolidin-3-ylmethyl}-amino)-piperidin-1-yl]-benzonitrile

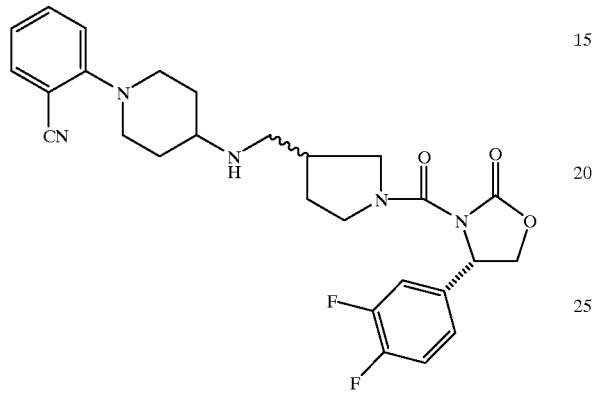

$^1$H NMR (CDCl$_3$, 400 MHz) consistent with assigned structure.

FABLRMS m/e 510 g/mole (M$^+$+H, C$_{27}$H$_{29}$F$_2$N$_5$O$_3$= 509.55 g/mole.)

HPLC (Vydac; C18; diameter=4.6 mm; length=150 mm; gradient=H$_2$O [0.1% H$_3$PO$_4$] —CH$_3$CN, 95%–5%, 5%–95%, over 16 minutes, 2 ml/min flow rate) focus=215 nm; 100% pure.

Anal. Calcd for C$_{27}$H$_{29}$F$_2$N$_5$O$_3$: C=57.16, H=5.84, N=11.11. Found: C=57.24, H=5.78, N=11.12.

EXAMPLE 26
(4S)-3-(3-{[1-(2-Cyanophenyl)-piperidin-4-ylamino]-methyl}-pyrrolidine-1-carbonyl)-4-(3,4-difluorophenyl)-6-methoxymethyl-2-oxo-1,2,3,4-tetrahydro-pyrimidine-5-carboxylic acid methyl ester

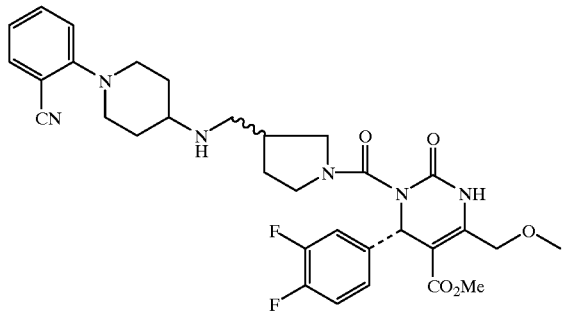

$^1$H NMR (CDCl$_3$, 400 MHz) consistent with assigned structure.

FABLRMS m/e 623 g/mole (M$^+$+H, C$_{32}$H$_{36}$F$_2$N$_6$O$_5$= 622.67 g/mole.)

HPLC (Vydac; C18; diameter=4.6 mm; length=150 mm; gradient=H$_2$O [0.1% H$_3$PO$_4$] —CH$_3$CN, 95%–5%, 5%–95%, over 16 minutes, 2 ml/min flow rate) focus=215 nm; 95.3% pure.

Anal. Calcd for C$_{32}$H$_{36}$F$_2$N$_6$O$_5$. 1.3 HCl and 0.55 H$_2$O: C=56.62, H=5.69, N=12.36. Found: C=56.53, H=5.69, N=12.32.

Examples 27 and 28 were prepared as outlined in Scheme 9.

EXAMPLE 27
(racemic) (4S)-2-[4-({1-[4-(3,4-Difluorophenyl)-2-oxo-oxazolidine-3-carbonyl]-3-hydroxy-pyrrolidin-4-yl}-amino)-piperidin-1-yl]-benzonitrile

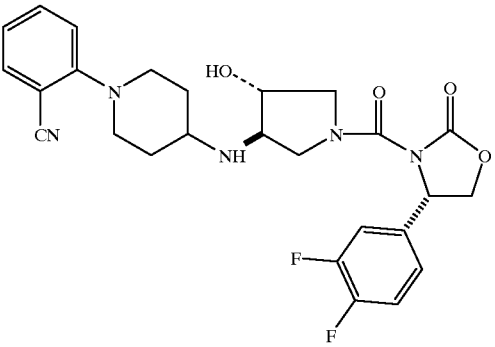

$^1$H NMR (CDCl$_3$, 400 MHz) consistent with assigned structure.

FABLRMS m/e 501.2 g/mole (M$^+$+H, C$_{26}$H$_{30}$F$_2$N$_4$O$_4$= 500.54 g/mole.)

HPLC (Vydac; C18; diameter=4.6 mm; length=150 mm; gradient=H$_2$O [0.1% H$_3$PO$_4$] —CH$_3$CN, 95%–5%, 5%–95%, over 16 minutes, 2 ml/min flow rate) focus=215 nm; 87% pure.

EXAMPLE 28
(racemic) (4S)-3-(4-[1-(2-Cyanophenyl)-piperidin-4-ylamino]-3-hydroxy-pyrrolidine-1-carbonyl)-4-(3,4-difluorophenyl )-6-methoxymethyl-2-oxo-1,2,3,4-tetrahydro-pyrimidine-5-carboxylic acid methyl ester

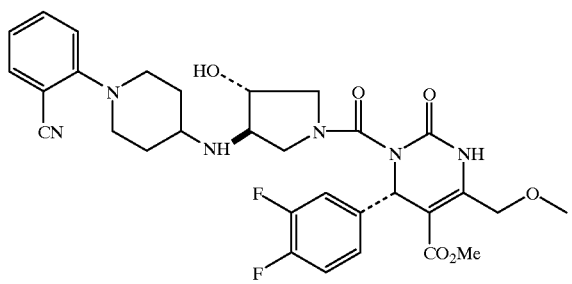

$^1$H NMR (CDCl$_3$, 400 MHz) consistent with assigned structure.

FABLRMS m/e 625.88 g/mole (M$^+$+H, C$_{31}$H$_{34}$F$_2$N$_6$O$_6$= 624.65 g/mole.)

HPLC (Vydac; C18; diameter=4.6 mm; length=150 mm; gradient=H$_2$O [0.1% H$_3$PO$_4$] —CH$_3$CN, 95%–5%, 5%–95%, over 16 minutes, 2 ml/min flow rate) focus=215 nm; 98% pure.

EXAMPLE 29
As a specific embodiment of an oral composition, 100 mg of the compound of Example 9 (i.e., Compound 14) is formulated with sufficient finely divided lactose to provide a total amount of 580 to 590 mg to fill a size 0 hard gel capsule.

EXAMPLE 30
Screening assay: Alpha 1a Adrenergic Receptor Binding

Membranes prepared from the stably transfected human alpha 1a cell line (ATCC CRL 11140) were used to identify compounds that bind to the human alpha 1a adrenergic receptor. These competition binding reactions (total volume=200 R1) contained 50 mM Tris-HCl pH. 7.4, 5 mM EDTA, 150 mM NaCl, 100 pM [$^{125}$I]-HEAT, membranes prepared from the alpha 1a cell line and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki). Representative compounds of the present invention were found to have Ki values $\leq$50 nM.

EXAMPLE 31
Selective Binding assays

Membranes prepared from stably transfected human alpha 1d and alpha 1b cell lines (ATCC CRL 11138 and CRL 11139, respectively) were used to identify compounds that selectively bind to the human alpha 1a adrenergic receptor. These competition binding reactions (total volume=200 $\mu$l) contained 50 mM Tris-HCl pH. 7.4, 5 mM EDTA, 150 mM NaCl, 100 $\mu$M [125 I]-HEAT, membranes prepared from cell lines transfected with the respective alpha 1 subtype expression plasmid and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki).

EXAMPLE 32
Exemplary Counterscreens
1. Assay Title: Dopamine D2, D3, D4 in vitro screen
Objective of the Assay:

The objective of this assay is to eliminate agents which specifically affect binding of [3H] spiperone to cells expressing human dopamine receptors D2, D3 or D4.
Method:

Modified from VanTol et al (1991); Nature (Vol 350) Pg 610–613.

Frozen pellets containing specific dopamine receptor subtypes stably expressed in clonal cell lines are lysed in 2 ml lysing buffer (10 mM Tris-HCV/5mM Mg, pH 7.4). Pellets obtained after centrifuging these membranes (15' at 24,450 rpm) are resuspended in 50 mM Tris-HCl pH 7.4 containing EDTA, MgCl[2], KCl, NaCl, CaCl[2] and ascorbate to give a 1 Mg/mL suspension. The assay is initiated by adding 50–75 $\mu$g membranes in a total volume of 500 $\mu$l containing 0.2 nM [3H]-spiperone. Non-specific binding is defined using 10 $\mu$M apomorphine. The assay is terminated after a 2 hour incubation at room temperature by rapid filtration over GF/B filters presoaked in 0.3% PEI, using 50 mM Tris-HCl pH 7.4.
2. Assay Title: Serotonin 5HT1a
Objective of the Assay The objective of this assay is to eliminate agents which specifically affect binding to cloned human 5HT1a receptor
Method:

Modified from Schelegel and Peroutka *Biochemical Pharmacology* 35: 1943–1949 (1986).

Mammalian cells expressing cloned human 5HT1a receptors are lysed in ice-cold 5 mM Tris-HCl, 2 mM EDTA (pH 7.4) and homogenized with a polytron homogenizer. The homogenate is centrifuged at 1000×g for 30', and then the supernatant is centrifuged again at 38,000×g for 30'. The binding assay contains 0.25 nM [3H]8-OH-DPAT (8-hydroxy-2-dipropylamino-1,2,3,4-tetrahydronaphthalene) in 50 mM Tris-HCl, 4 mM CaCl2 and 1 mg/ml ascorbate. Non-specific binding is defined using 10 $\mu$M propranolol. The assay is terminated after a 1 hour incubation at room temperature by rapid filtration over GF/Cfilters

EXAMPLE 33
Exemplary Functional Assays

In order to confirm the specificity of compounds for the human alpha 1a adrenergic receptor and to define the biological activity of the compounds, the following functional tests may be performed:
1. In vitro Rat, Dog and Human Prostate and Dog Urethra Taconic Farms Sprague-Dawley male rats, weighing 250–400 grams are sacrificed by cervical dislocation under anesthesia (methohexital; 50 mg/kg, i.p.). An incision is made into the lower abdomen to remove the ventral lobes of the prostate. Each prostate removed from a mongrel dog is cut into 6–8 pieces longitudinally along the urethra opening and stored in ice-cold oxygenated Krebs solution overnight before use if necessary. Dog urethra proximal to prostate is cut into approximately 5 mm rings, the rings are then cut open for contractile measurement of circular muscles. Human prostate chips from transurethral surgery of benign prostate hyperplasia are also stored overnight in ice-cold Krebs solution if needed.

The tissue is placed in a Petri dish containing oxygenated Krebs solution [NaCl, 118 mM; KCl, 4.7 mM; CaCl$_2$, 2.5 mM; KH$_2$PO$_4$, 1.2 mM; MgSO$_4$, 1.2 mM; NaHCO$_3$, 2.0 mM; dextrose, 11 mM] warmed to 37° C. Excess lipid material and connective tissue are carefully removed. Tissue segments are attached to glass tissue holders with 4-0 surgical silk and placed in a 5 ml jacketed tissue bath containing Krebs buffer at 37° C., bubbled with 5% CO$_2$/95% O$_2$. The tissues are connected to a Statham-Gould force transducer; 1 gram (rat, human) or 1.5 gram (dog) of tension is applied and the tissues are allowed to equilibrate for one hour. Contractions are recorded on a Hewlett-Packard 7700 series strip chart recorder.

After a single priming dose of 3 $\mu$M (for rat), 10 $\mu$M (for dog) and 20 $\mu$M (for human) of phenylephrine, a cumulative concentration response curve to an agonist is generated; the tissues are washed every 10 minutes for one hour. Vehicle or antagonist is added to the bath and allowed to incubate for one hour, then another cumulative concentration response curve to the agonist is generated.

EC50 values are calculated for each group using Graph-Pad Inplot software. pA$_2$ (-log Kb) values were obtained from Schild plot when three or more concentrations were tested. When less than three concentrations of antagonist are tested, Kb values are calculated according to the following formula $$K_b = \frac{[B]}{x-1},$$

where x is the ratio of EC50 of agonist in the presence and absence of antagonist and [B] is the antagonist concentration.
2. Measurement of Intra-Urethral Pressure in Anesthetized Dogs
Purpose:

Benign prostatic hyperplasia causes a decreased urine flow rate that may be produced by both passive physical obstruction of the prostatic urethra from increased prostate mass as well as active obstruction due to prostatic contraction. Alpha adrenergic receptor antagonists such as prazosin and terazosin prevent active prostatic contraction, thus improve urine flow rate and provide symptomatic relief in man. However, these are non-selective alpha 1 receptor antagonists which also have pronounced vascular effects. Because we have identified the alpha 1a receptor subtype as the predominent subtype in the human prostate, it is now possible to specifically target this receptor to inhibit prostatic contraction without concomitant changes in the vasculature. The following model is used to measure adrenergically mediated changes in intra-urethral pressure and arterial pressure in anesthetized dogs in order to evaluate the efficacy and potency of selective alpha adrenergic receptor antagonists. The goals are to: 1) identify the alpha 1 receptor subtypes responsible for prostatic/urethral contraction and vascular responses, and 2) use this model to evaluate novel selective alpha adrenergic antagonists. Novel and standard alpha adrenergic antagonists may be evaluated in this manner.

Methods:

Male mongrel dogs (7–12 kg) are used in this study. The dogs are anesthetized with pentobarbital sodium (35 mg/kg, i.v. plus 4 mg/kg/hr iv infusion). An endotracheal tube is inserted and the animal ventilated with room air using a Harvard instruments positive displacement large animal ventilator. Catheters (PE 240 or 260) are placed in the aorta via the femoral artery and vena cava via the femoral veins (2 catheters, one in each vein) for the measurement of arterial pressure and the administration of drugs, respectively. A supra-pubic incision ~½ inch lateral to the penis is made to expose the urethers, bladder and urethra. The urethers are ligated and cannulated so that urine flows freely into beakers. The dome of the bladder is retracted to facilitate dissection of the proximal and distal urethra. Umbilical tape is passed beneath the urethra at the bladder neck and another piece of umbilical tape is placed under the distal urethra approximately 1–2 cm distal to the prostate. The bladder is incised and a Millar micro-tip pressure transducer is advanced into the urethra. The bladder incision is sutured with 2-0 or 3-0 silk (purse-string suture) to hold the transducer. The tip of the transducer is placed in the prostatic urethra and the position of the Millar catheter is verified by gently squeezing the prostate and noting the large change in urethral pressure.

Phenylephrine, an alpha 1 adrenergic agonist, is administered (0.1–100 ug/kg, iv; 0.05 ml/kg volume) in order to construct dose response curves for changes in intra-urethral and arterial pressure. Following administration of increasing doses of an alpha adrenergic antagonist (or vehicle), the effects of phenylephrine on arterial pressure and intra-urethral pressure are re-evaluated. Four or five phenylephrine dose-response curves are generated in each animal (one control, three or four doses of antagonist or vehicle). The relative antagonist potency on phenylephrine induced changes in arterial and intra-urethral pressure are determined by Schild analysis. The family of averaged curves are fit simultaneously (using ALLFIT software package) with a four paramenter logistic equation constraining the slope, minimum response, and maximum response to be constant among curves. The dose ratios for the antagonist doses (rightward shift in the dose-response curves from control) are calculated as the ratio of the $ED_{50}$'s for the respective curves. These dose-ratios are then used to construct a Schild plot and the Kb (expressed as ug/kg, iv) determined. The Kb (dose of antagonist causing a 2-fold rightward shift of the phenylephrine dose-response curve) is used to compare the relative potency of the antagonists on inhibiting phenylephrine responses for intra-urethral and arterial pressure. The relative selectivity is calculated as the ratio of arterial pressure and intra-urethral pressure Kb's. Effects of the alpha 1 antagonists on baseline arterial pressure are also monitored. Comparison of the relative antagonist potency on changes in arterial pressure and intra-urethral pressure provide insight as to whether the alpha receptor subtype responsible for increasing intra-urethral pressure is also present in the systemic vasculature. According to this method, one is able to confirm the selectivity of alpha 1a adrenergic receptor antagonists that prevent the increase in intra-urethral pressure to phenylephrine without any activity at the vasculature.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of the formula:

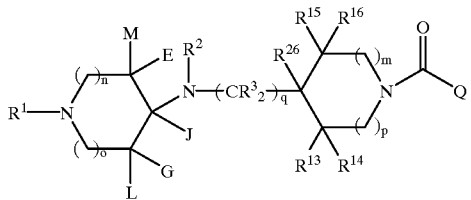

wherein Q is $R^1$ is selected from unsubstituted, mono- or poly-substituted phenyl wherein the substituents on the phenyl are independently selected from halogen, $CF_3$, cyano, nitro, $N(R^7)_2$, $NR^7COR^{19}$, $NR^7CON(R^{19})_2$, $NR^7SO_2R^{19}$, $NR^7SO_2N(R^{19})_2$, $OR^6$, $(CH_2)_{0-4}CO_2R^7$, $(CH_2)_{0-4}CON(R^7)_2$, or $C_{1-4}$ alkyl; or unsubstituted, mono- or poly-substituted pyridyl, pyrazinyl, thienyl, thiazolyl, furanyl, quinazolinyl or naphthyl wherein the substituents on the pyridyl, pyrazinyl, thienyl, thiazolyl, furanyl, quinazolinyl or naphthyl are independently selected from $CF_3$, cyano, nitro, amino, $(CH_2)_{0-4}CO_2R^7$, $(CH_2)_{0-4}CON(R^7)_2$, $(CH_2)_{0-4}SO_2N(R^7)_2$, $(CH_2)_{0-4}SO_2R^6$, phenyl, $OR^6$, halogen, $C_{1-4}$ alkyl or $C_{3-8}$ cycloalkyl;

E, G, L and M are each independently selected from hydrogen, $C_{1-8}$ alkyl, $C_{3-8}$ cycloalkyl, $(CH_2)_{0-4}OR^6$, $(CH_2)_{0-4}N(R^7)_2$, $(CH_2)_{0-4}CN$, $(CH_2)_{0-4}CF_3$, $(CH_2)_{0-4}CO_2R^7$, $(CH_2)_{0-4}CON(R^7)_2$, $(CH_2)_{0-4}SO_2R^7$, or $(CH_2)_{0-4}SO_2N(R^7)_2$;

J is selected from hydrogen, $C_{1-8}$ alkyl, $C_{3-8}$ cycloalkyl, $(CH_2)_{1-4}OR^6$, $(CH_2)_{1-4}N(R^7)_2$, $(CH_2)_{1-4}CN$, $(CH_2)_{0-4}CF_3$, $(CH_2)_{0-4}CO_2R^7$, $(CH_2)_{04}CON(R^7)_2$, $(CH_2)_{0-4}SO_2R^7$, or $(CH_2)_{0-4}SO_2N(R^7)_2$;

$R^2$ is independently selected from hydrogen, $C_{1-8}$ alkyl, $C_{4-8}$ cycloalkyl, $(CH_2)_{04}CO_2R^7$, $(CH_2)_{0-4}CON(R^7)_2$, $(CH_2)_{0-4}COR^7$, $(CH_2)_{2-4}OR^6$, $(CH_2)1–4CF_3$, $(CH_2)_{0-4}SO_2R^7$, $(CH_2)_{0-4}SO_2N(R^7)_2$ or $(CH_2)_{1-4}CN$;

$R^3$, $R^8$, $R^{14}$, $R^{15}$ and $R^{16}$ are each independently selected from hydrogen, $C_{1-8}$ alkyl, $C_{3-8}$ cycloalkyl, $(CH_2)_{2-4}OR^6$ or $(CH_2)_{0-4}CF_3$;

$R^4$ is selected from hydrogen, $(CH_2)_{0-4}COR^6$, $(CH_2)_{0-4}CN$, $(CH_2)_{0-4}CF_3$, $(CH_2)_{0-4}CO_2R^7$, $(CH_2)_{0-4}CON(R^7)_2$, $(CH_2)_{0-4}SO_2R^6$, or $(CH_2)_{0-4}SO_2N(R^7)_2$;

$R^5$ is selected from hydrogen, $C_{1-8}$ alkyl, $C_{3-8}$ cycloalkyl, $(CH_2)_{1-4}OR^6$ or $(CH_2)_{0-4}CF_3$;

$R^6$ is selected from hydrogen, $C_{1-8}$ alkyl, $C_{3-8}$ cycloalkyl or $(CH_2)_{0-4}CF_3$;

$R^7$ and $R^{19}$ are each independently selected from hydrogen, $C_{1-8}$ alkyl, $C_{4-8}$ cycloalkyl or $(CH_2)_{1-4}CF_3$;

$R^{11}$ and $R^{12}$ are each independently selected from hydrogen, $C_{1-8}$ alkyl or $C_{3-8}$ cycloalkyl;

$R^{13}$ is selected from hydrogen, $C_{1-8}$ alkyl, $C_{3-8}$ cycloalkyl, $(CH_2)_{2-4}OR^6$, $OR^6$ or $(CH_2)_{0-4}CF_3$;

W is O or $NR^{11}$;

$R^{26}$ is selected from hydrogen or $OR^{28}$;

$R^{28}$ is selected from hydrogen, $C_{1-8}$ alkyl, $C_{3-8}$ cycloalkyl, $(CH_2)_{2-4}OR^6$ or $(CH_2)_{0-4}CF_3$;

X is selected from halogen, cyano, nitro, $C_{1-8}$ alkyl $C_{3-8}$ cycloalkyl, $(CH_2)_{0-4}OR^6$ or $(CH_2)_{0-4}CF_3$ m and p are each integers from zero to two, wherein the sum m+p=2;

n and o are each integers from zero to two, wherein the sum n+o=2;

q is an integer of from zero to three, provided that when q is zero, $R^{26}$ is hydrogen; and s is an integer of from zero to four;

or a pharmaceutically acceptable salt thereof.

2. The compound of claim 1 of the formula:

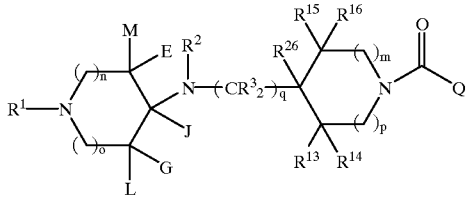

wherein $R^4$ is selected from $(CH_2)_{0-4}COR^6$, $(CH_2)_{0-4}CN$, $(CH_2)_{0-4}CF_3$, $(CH_2)_{0-4}CO_2R^7$, $(CH_2)_{0-4}CON(R^7)_2$, $(CH_2)_{0-4}SO_2R^6$, or $(CH_2)_{0-4}SO_2N(R^7)_2$; and $R^{13}$ is selected from hydrogen, $C_{1-8}$ alkyl, $C_{3-8}$ cycloalkyl, $(CH_2)_{2\ 4}OR^6$ or $(CH_2)_{0-4}CF_3$;

or a pharmaceutically acceptable salt thereof.

3. The compound of claim 1 of the formula:

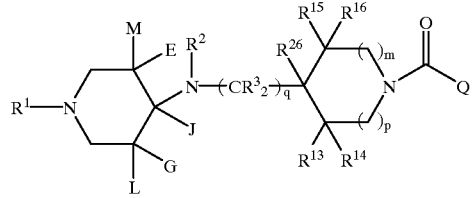

wherein Q is

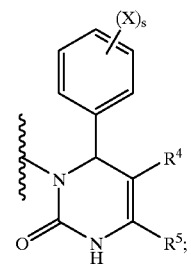

$R^1$ is selected from unsubstituted, mono-, di- or tri-substituted phenyl wherein the substituents on the phenyl are independently selected from halogen, $CF_3$, cyano, nitro, $N(R^7)_2$, $NR^7COR^{19}$, $NR^7CON(R^{19})_2$, $NR^7SO_2R^{19}$, $NR^7SO_2N(R^{19})_2$, $OR^6$, $(CH_2)_{0-4}CO_2R^7$, $(CH_2)_0$—$CON(R^7)_2$, or $C_{1-4}$ alkyl; or unsubstituted, mono-, di- or tri-substituted pyridyl, pyrazinyl, thienyl, thiazolyl, furanyl, quinazolinyl or naphthyl wherein the substituents on the pyridyl, pyrazinyl, thienyl, thiazolyl, furanyl, quinazolinyl or naphthyl are independently selected from $CF_3$, cyano, nitro, amino, $(CH_2)_{0-4}CO_2R^7$, $(CH_2)_{0-4}CON(R^7)_2$, $(CH_2)_{0-4}SO_2N(R^7)_2$, $(CH_2)_{0-4}SO_2R^6$, phenyl, $OR^6$, halogen, $C_{1-4}$ alkyl or $C_{3-8}$ cycloalkyl;

E, G, L, M and J are each independently selected from hydrogen, $C_{1-8}$ alkyl, $C_{3-8}$ cycloalkyl, or $(CH_2)_{0-4}CF_3$;

$R^2$ is selected from hydrogen, $C_{1-8}$ alkyl, $C_{4-8}$ cycloalkyl or $(CH_2)_{1-4}CF_3$;

$R^3$, $R^{14}$, $R^{15}$ and $R^{16}$ are each independently selected from hydrogen, $C_{1-6}$ alkyl, $C_{3-6}$ cycloalkyl, $(CH_2)_{2-4}OR^6$ or $(CH_2)_{0-4}CF_3$;

$R^{13}$ is selected from hydrogen, $C_{1-6}$ alkyl, $C_{3-6}$ cycloalkyl, $(CH_2)_{2-4}OR^6$, $OR^6$ or $(CH_2)_{0-4}CF_3$; and $R^{28}$ is selected from hydrogen, $C_{1-6}$ alkyl, $C_{3-6}$ cycloalkyl, $(CH_2)_{2-4}OR^6$, or $(CH_2)_{0-4}CF_3$;

or a pharmaceutically acceptable salt thereof.

4. The compound of claim 3, of the formula

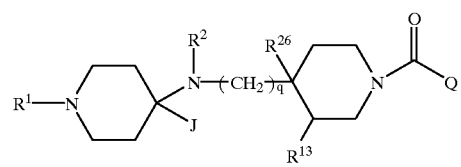

wherein Q is

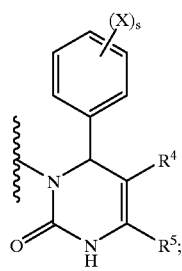

$R^1$ is selected from unsubstituted, mono-, di or tri-substituted phenyl wherein the substituents on the phenyl are independently selected from halogen, $CF_3$, cyano, nitro, $N(R^7)_2$, $OR^6$, $(CH_2)_{0-2}CO_2R^7$, $(CH_2)_{0-2}CON(R^7)_2$, or $C_{1-4}$ alkyl; or unsubstituted, mono- or di-substituted pyridyl wherein the substituents are independently selected from halogen, $CF_3$, cyano, nitro, amino, $OR^6$, $CO_2R^7$, $CON(R^7)_2$ or $C_{1-4}$ alkyl;

$R^2$ is selected from hydrogen, $C_{1-6}$ alkyl, $C_{4-6}$ cycloalkyl or $(CH_2)_{1-4}CF_3$;

$R^4$ is selected from hydrogen, $COR^6$, $(CH_2)_{0-2}CO_2R^7$, $O_2R^6$ or $(CH_2)_{0-2}CON(R^7)_2$;

$R^5$ is selected from hydrogen, $C_{1-6}$ alkyl, $C_{3-6}$ cycloalkyl, $(CH_2)_{1-3}OR^6$ or $(CH_2)_{0-3}CF_3$; and $R^6$ is selected from hydrogen, $C_{1-6}$ alkyl, $C_{3-6}$ cycloalkyl or $(CH_2)_{0-2}CF_3$;

$R^7$ is selected from hydrogen, $C_{1-6}$ alkyl, $C_{4-6}$ cycloalkyl or $(CH_2)_{1-2}CF_3$;

$R^{13}$ is selected from hydrogen or $OR^6$; and $R^{26}$ is selected from hydrogen or $OR^{28}$, wherein $R^{28}$ is selected from hydrogen or $C_{1-6}$ alkyl;

or a pharmaceutically acceptable salt thereof.

5. The compound of claim 4, of the formula

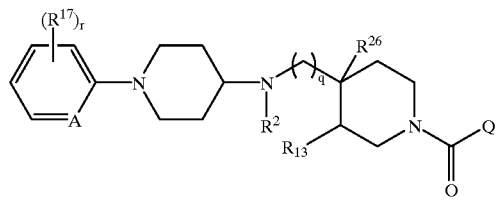

wherein A is $C—R^{17}$ or N;

$R^2$ is selected from hydrogen or $CH_2CF_3$;

$R^{13}$ is selected from hydrogen or hydroxy;

each $R^{17}$ is independently selected from hydrogen, halogen, $CF_3$, cyano, nitro, amino, $OR^6$, $CO_2R^7$, $CON(R^7)_2$ or $C_{1-4}$ alkyl;

$R^{26}$ is selected from hydrogen or hydroxy;

each X is halogen;

q and r are each independently an integer from zero to two, provided that when q is zero, $R^{26}$ is hydrogen; and s is an integer from zero to three;

or a pharmaceutically acceptable salt thereof.

6. The compound of claim 5, which is

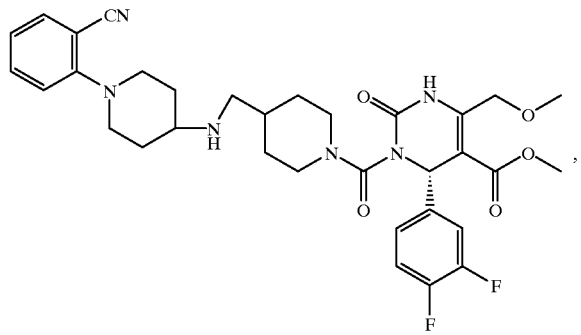

or a pharmaceutically acceptable salt thereof.

7. A pharmaceutical composition comprising the compound of claim 1 and a pharmaceutically acceptable carrier.

8. A method of treating benign prostatic hyperplasia in a subject in need thereof which comprises administering to the subject a therapeutically effective amount of the compound of claim 1.

9. The method of claim 8, wherein the therapeutically effective amount of the compound additionally does not cause hypotension.

10. A method of treating benign prostatic hyperplasia in a subject in need thereof which comprises administering a therapeutically effective amount of the composition of claim 7.

11. A method of relaxing lower urinary tract tissue in a subject in need thereof which comprises administering to the subject a therapeutically effective amount of the compound of claim 1.

12. The method of claim 11, wherein the therapeutically effective amount of the compound additionally does not cause hypotension.

13. A process for making a pharmacuetical composition comprising combining a compound of claim 1 and a pharmaceutically acceptable carrier.

* * * * *